United States Patent
Sharkey et al.

(10) Patent No.: US 7,069,087 B2
(45) Date of Patent: Jun. 27, 2006

(54) APPARATUS AND METHOD FOR ACCESSING AND PERFORMING A FUNCTION WITHIN AN INTERVERTEBRAL DISC

(75) Inventors: Hugh R. Sharkey, Menlo Park, CA (US); Sepehr Fariabi, Fremont, CA (US); John Ashley, San Fancisco, CA (US); Joel Saal, Portola Valley, CA (US); Jeffrey Saal, Portola Valley, CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/792,628

(22) Filed: Feb. 22, 2001

(65) Prior Publication Data

US 2002/0022830 A1 Feb. 21, 2002

Related U.S. Application Data

(60) Provisional application No. 60/185,221, filed on Feb. 25, 2000.

(51) Int. Cl.
*A61F 7/00* (2006.01)
*A61F 2/00* (2006.01)
*A61B 18/18* (2006.01)

(52) U.S. Cl. ............................ 607/76; 606/15; 607/101; 607/89

(58) Field of Classification Search .................. 607/96, 607/97, 98, 99, 100, 101, 102; 600/434; 604/164.13, 604/528, 529
See application file for complete search history.

(56) References Cited

U.S. PATENT DOCUMENTS

| 2,090,923 A | 8/1937 | Wappler | 128/303.15 |
|---|---|---|---|
| 3,178,728 A | 4/1965 | Christensen | 3/1 |
| 3,579,643 A | 5/1971 | Morgan | 3/1 |
| 3,776,230 A | 12/1973 | Neefe | 128/260 |
| 3,856,015 A | 12/1974 | Iglesias | 128/303.15 |
| 3,867,728 A | 2/1975 | Substad et al. | 3/1 |
| 3,879,767 A | 4/1975 | Substad | 3/1 |

(Continued)

FOREIGN PATENT DOCUMENTS

| CA | 2188688 | 11/1995 |
|---|---|---|
| DE | 3 511 107 A1 | 10/1986 |
| DE | 3632197 A1 | 3/1988 |
| EP | 0 257 116 A1 | 3/1988 |
| EP | 0 274 705 A1 | 7/1988 |
| EP | 0 479 482 A1 | 4/1992 |
| EP | 0 521 595 A2 | 1/1993 |

(Continued)

*Primary Examiner*—Roy D. Gibson
(74) *Attorney, Agent, or Firm*—Fish & Richardson P.C.

(57) ABSTRACT

Apparatus and methods are disclosed for accessing the interior of an intervertebral disc to perform a function within the disc. One such apparatus comprises a catheter having a lumen; and a guide wire having a distal portion and a proximal portion, and configured to be positioned within and moved relative to the lumen of the catheter; wherein the guide wire is capable of navigating itself within an intradiscal section of the intervertebral disc to a selected section of the disc and the catheter is capable of being advanced relative to the guide wire such that the catheter follows a path of the guide wire within the intradiscal section of the disc to the selected section. These apparatus and methods may be used for the treatment of intervertebral disc disorders such as sealing fissures of the annulus fibrosus, which may or may not be accompanied with contained or escaped extrusions. These apparatus and methods may also be used, for example, for the removal or addition of material to the intervertebral disc.

48 Claims, 24 Drawing Sheets

U.S. PATENT DOCUMENTS

| | | |
|---|---|---|
| 3,886,600 A | 6/1975 | Kahn et al. ............................ 3/1 |
| 3,938,198 A | 2/1976 | Kahn et al. .................... 3/1.912 |
| 3,945,375 A | 3/1976 | Banko ............................... 128/6 |
| 3,987,499 A | 10/1976 | Scharbach et al. ............. 3/1.91 |
| 3,992,725 A | 11/1976 | Homsy ................................. 3/1 |
| 4,043,342 A | 8/1977 | Morrison, Jr. .......... 128/303.14 |
| 4,074,718 A | 2/1978 | Morrison, Jr. .......... 128/303.14 |
| 4,085,466 A | 4/1978 | Goodfellow et al. ........... 3/1.91 |
| 4,129,470 A | 12/1978 | Homsy ........................ 156/155 |
| 4,134,406 A | 1/1979 | Iglesias ................. 128/303.15 |
| 4,224,696 A | 9/1980 | Murray et al. ................ 3/1.911 |
| 4,224,697 A | 9/1980 | Murray et al. ................ 3/1.911 |
| 4,326,529 A | 4/1982 | Doss et al. ............... 128/303.1 |
| 4,344,193 A | 8/1982 | Kenny .......................... 3/1.911 |
| 4,362,160 A | 12/1982 | Hiltebrandt ............. 128/303.15 |
| 4,375,220 A | 3/1983 | Matvias ....................... 128/804 |
| 4,381,007 A | 4/1983 | Doss ......................... 128/303.1 |
| 4,397,314 A | 8/1983 | Vaguine ........................ 128/399 |
| 4,476,862 A | 10/1984 | Pao ........................ 128/303.17 |
| 4,483,338 A | 11/1984 | Bloom et al. ........... 128/303.13 |
| 4,517,965 A | 5/1985 | Ellison ........................ 128/20 |
| 4,517,975 A | 5/1985 | Garito et al. ........... 128/303.13 |
| 4,590,934 A | 5/1986 | Malis et al. ............. 128/303.14 |
| 4,593,691 A | 6/1986 | Lindstrom et al. ..... 128/303.14 |
| 4,597,379 A | 7/1986 | Kihn et al. .................. 128/1 R |
| 4,601,705 A | 7/1986 | McCoy ........................ 604/94 |
| 4,651,734 A | 3/1987 | Doss et al. ............. 128/303.14 |
| 4,811,733 A | 3/1989 | Borsanyi et al. ........ 128/303.14 |
| 4,815,462 A | 3/1989 | Clark ........................... 128/305 |
| 4,838,859 A | 6/1989 | Strassmann .................... 604/95 |
| 4,846,175 A | 7/1989 | Frimberger |
| 4,873,976 A | 10/1989 | Schreiber ................ 128/334 R |
| 4,895,148 A | 1/1990 | Bays et al. .................. 606/213 |
| 4,907,585 A | 3/1990 | Schachar ...................... 606/28 |
| 4,907,589 A | 3/1990 | Cosman ........................ 606/34 |
| 4,924,865 A | 5/1990 | Bays et al. .................... 606/77 |
| 4,944,727 A | 7/1990 | McCoy ......................... 604/95 |
| 4,950,234 A | 8/1990 | Fujioka et al. ................. 604/60 |
| 4,950,267 A | 8/1990 | Ishihara et al. |
| 4,955,882 A | 9/1990 | Hakky ........................ 606/14 |
| 4,966,597 A | 10/1990 | Cosman ........................ 606/50 |
| 4,976,709 A | 12/1990 | Sand .............................. 606/5 |
| 4,976,715 A | 12/1990 | Bays et al. .................... 606/77 |
| 4,984,063 A | 1/1991 | Terashima ..................... 623/13 |
| 4,998,933 A | 3/1991 | Eggers et al. ................. 606/41 |
| 5,007,908 A | 4/1991 | Rydell .......................... 606/47 |
| 5,009,656 A | 4/1991 | Reimels ........................ 606/48 |
| 5,084,043 A | 1/1992 | Hertzmann et al. |
| 5,085,657 A | 2/1992 | Ben-Simhon ................ 606/42 |
| 5,085,659 A | 2/1992 | Rydell .......................... 606/47 |
| 5,098,430 A | 3/1992 | Fleenor ........................ 606/42 |
| 5,100,402 A | 3/1992 | Fan ............................... 606/41 |
| 5,103,804 A | 4/1992 | Abele et al. .................... 128/4 |
| 5,114,402 A | 5/1992 | McCoy |
| 5,152,748 A | 10/1992 | Chastagner |
| 5,178,620 A | 1/1993 | Eggers et al. ................. 606/41 |
| 5,186,181 A | 2/1993 | Franconi et al. ............ 128/804 |
| 5,191,883 A | 3/1993 | Lennox et al. ............... 128/401 |
| 5,192,267 A | 3/1993 | Shapira et al. ................ 604/22 |
| 5,201,729 A | 4/1993 | Hertzmann et al. ........... 606/2 |
| 5,201,730 A | 4/1993 | Easley et al. .................. 606/4 |
| 5,201,731 A | 4/1993 | Hakky .......................... 606/15 |
| 5,213,097 A | 5/1993 | Zeindler ..................... 128/401 |
| 5,230,334 A | 7/1993 | Klopotek ..................... 128/399 |
| 5,242,439 A | 9/1993 | Larsen et al. ................. 606/15 |
| 5,242,441 A | 9/1993 | Avitall .......................... 606/41 |
| 5,261,906 A | 11/1993 | Pennino et al. .............. 606/46 |
| 5,267,994 A | 12/1993 | Gentelia et al. .............. 606/15 |
| 5,275,151 A | 1/1994 | Shockey et al. .............. 128/4 |
| 5,279,559 A | 1/1994 | Barr |
| 5,284,479 A | 2/1994 | de Jong ........................ 604/60 |
| 5,304,169 A | 4/1994 | Sand .............................. 606/5 |
| 5,308,311 A | 5/1994 | Eggers et al. ................. 606/28 |
| 5,311,858 A | 5/1994 | Adair ............................ 128/4 |
| 5,320,115 A | 6/1994 | Kenna ........................ 128/898 |
| 5,323,778 A | 6/1994 | Kandarpa et al. ......... 128/653.2 |
| 5,334,193 A | 8/1994 | Nardella ....................... 606/41 |
| 5,342,357 A | 8/1994 | Nardella ....................... 606/40 |
| 5,348,554 A | 9/1994 | Imran et al. ................... 606/41 |
| 5,352,868 A | 10/1994 | Denen et al. ................ 219/501 |
| 5,354,331 A | 10/1994 | Schachar ........................ 623/4 |
| 5,364,395 A | 11/1994 | West, Jr. ....................... 606/46 |
| 5,366,443 A | 11/1994 | Eggers et al. ............... 604/114 |
| 5,366,490 A | 11/1994 | Edwards et al. ............. 607/99 |
| 5,382,247 A | 1/1995 | Cimino et al. ................ 606/33 |
| 5,397,304 A | 3/1995 | Truckai ......................... 604/95 |
| 5,401,272 A | 3/1995 | Perkins ......................... 606/15 |
| 5,415,633 A | 5/1995 | Lazarus et al. ................ 604/95 |
| 5,423,806 A | 6/1995 | Dale et al. ..................... 606/15 |
| 5,433,739 A | 7/1995 | Sluijter et al. ................. 607/99 |
| 5,437,661 A | 8/1995 | Rieser .......................... 606/15 |
| 5,437,662 A | 8/1995 | Nardella ....................... 606/40 |
| 5,451,223 A | 9/1995 | Ben-Simhon ................ 606/42 |
| 5,458,596 A | 10/1995 | Lax et al. ...................... 606/31 |
| 5,464,023 A | 11/1995 | Viera .......................... 128/772 |
| 5,465,737 A | 11/1995 | Schachar .................... 128/898 |
| 5,472,426 A | 12/1995 | Bonati et al. |
| 5,484,403 A | 1/1996 | Yoakum et al. ............... 604/59 |
| 5,484,432 A | 1/1996 | Sand .............................. 606/5 |
| 5,484,435 A | 1/1996 | Fleenor et al. ................ 606/46 |
| 5,487,757 A | 1/1996 | Truckai et al. .............. 607/122 |
| 5,498,258 A | 3/1996 | Hakky et al. ................. 606/15 |
| 5,500,012 A | 3/1996 | Brucker et al. ............. 607/122 |
| 5,507,812 A | 4/1996 | Moore ......................... 623/13 |
| 5,514,130 A | 5/1996 | Baker .......................... 606/41 |
| 5,520,645 A | 5/1996 | Imran et al. |
| 5,524,338 A | 6/1996 | Martyniuk et al. ........... 29/825 |
| 5,527,331 A | 6/1996 | Kresch et al. |
| 5,542,920 A | 8/1996 | Cherif Cheikh ............. 604/57 |
| 5,569,242 A | 10/1996 | Lax et al. ...................... 606/42 |
| 5,582,609 A | 12/1996 | Swanson et al. |
| 5,599,346 A | 2/1997 | Edwards et al. .............. 606/41 |
| 5,630,839 A | 5/1997 | Corbett, III et al. ......... 607/137 |
| 5,673,707 A | 10/1997 | Chandrasekaran |
| 5,681,282 A | 10/1997 | Eggers et al. ............... 604/114 |
| 5,683,366 A | 11/1997 | Eggers et al. ............... 604/114 |
| 5,688,270 A | 11/1997 | Yates et al. ................... 606/51 |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. ............... 604/114 |
| 5,718,702 A | 2/1998 | Edwards ...................... 606/41 |
| 5,762,629 A * | 6/1998 | Kambin ................... 604/164.11 |
| 5,782,795 A | 7/1998 | Bays ............................ 604/22 |
| 5,785,705 A | 7/1998 | Baker |
| 5,807,306 A | 9/1998 | Shapland et al. |
| 5,810,802 A | 9/1998 | Panescu et al. |
| 5,810,809 A | 9/1998 | Rydell .......................... 606/49 |
| 5,836,892 A * | 11/1998 | Lorenzo ...................... 600/433 |
| 5,836,947 A | 11/1998 | Fleischman et al. |
| 5,871,469 A | 2/1999 | Eggers et al. |
| 5,871,501 A * | 2/1999 | Leschinsky et al. ......... 606/213 |
| 5,882,346 A | 3/1999 | Pomeranz |
| 5,885,217 A * | 3/1999 | Gisselberg et al. .......... 600/434 |
| 5,885,278 A | 3/1999 | Fleischman et al. |
| 5,910,129 A | 6/1999 | Koblish et al. |
| 5,916,166 A * | 6/1999 | Reiss et al. .................. 600/434 |
| 5,980,471 A * | 11/1999 | Jafari .......................... 600/434 |
| 5,980,504 A | 11/1999 | Sharkey et al. |
| 5,993,424 A | 11/1999 | Lorenzo et al. |
| 6,004,319 A | 12/1999 | Goble et al. |

| | | | | | | |
|---|---|---|---|---|---|---|
| 6,007,570 A | * | 12/1999 | Sharkey et al. ............... 606/15 | EP | 0 558 297 A2 | 9/1993 |
| 6,010,493 A | | 1/2000 | Snoke | EP | 0 566 450 A1 | 10/1993 |
| 6,014,579 A | | 1/2000 | Pomeranz et al. | EP | 0 572 131 A1 | 12/1993 |
| 6,023,638 A | | 2/2000 | Swanson | EP | 0 682 910 A1 | 11/1995 |
| 6,033,397 A | | 3/2000 | Laufer et al. | EP | 0 479 482 B1 | 5/1996 |
| 6,048,329 A | | 4/2000 | Thompson et al. | EP | 0 729 730 A1 | 9/1996 |
| 6,056,744 A | | 5/2000 | Edwards | EP | 0 737 487 A2 | 10/1996 |
| 6,073,051 A | | 6/2000 | Sharkey et al. | EP | 0 783 903 A1 | 7/1997 |
| 6,095,149 A | | 8/2000 | Sharkey et al. | FR | 1122634 | 9/1956 |
| 6,099,514 A | | 8/2000 | Sharkey et al. | FR | 2 645 008 | 3/1989 |
| 6,106,522 A | | 8/2000 | Fleischman et al. | GB | 1 340 451 | 12/1973 |
| 6,122,549 A | | 9/2000 | Sharkey et al. | GB | 2 164 473 A | 3/1986 |
| 6,126,682 A | | 10/2000 | Sharkey et al. | JP | 5-42166 | 5/1993 |
| 6,135,999 A | | 10/2000 | Fanton et al. | SU | 637118 | 12/1978 |
| 6,165,139 A | * | 12/2000 | Damadian ................... 600/585 | WO | WO 82/02488 | 8/1982 |
| 6,203,525 B1 | | 3/2001 | Whayne et al. | WO | WO 85/02762 | 7/1985 |
| 6,217,528 B1 | | 4/2001 | Koblish et al. | WO | WO 92/05828 | 4/1992 |
| 6,224,592 B1 | | 5/2001 | Eggers et al. | WO | WO 92/10142 | 6/1992 |
| 6,241,754 B1 | | 6/2001 | Swanson et al. | WO | WO 93/01774 | 2/1993 |
| 6,245,061 B1 | | 6/2001 | Panescu et al. | WO | WO 93/16648 | 9/1993 |
| 6,258,086 B1 | | 7/2001 | Ashley et al. | WO | WO 93/20984 | 10/1993 |
| 6,261,311 B1 | | 7/2001 | Sharkey et al. | WO | WO 95/01814 | 1/1995 |
| 6,264,650 B1 | * | 7/2001 | Hovda et al. .................. 606/32 | WO | WO 95/10981 | 4/1995 |
| 6,264,651 B1 | * | 7/2001 | Underwood et al. .......... 606/32 | WO | WO 95/13113 | 5/1995 |
| 6,270,476 B1 | | 8/2001 | Santoianni et al. | WO | WO 95/18575 | 7/1995 |
| 6,273,886 B1 | | 8/2001 | Edwards et al. | WO | WO 95/20360 | 8/1995 |
| 6,283,960 B1 | | 9/2001 | Ashley | WO | WO 95/25471 | 9/1995 |
| 6,290,715 B1 | | 9/2001 | Sharkey et al. | WO | WO 95/30373 | 11/1995 |
| 6,308,091 B1 | | 10/2001 | Avitall | WO | WO 95/30377 | 11/1995 |
| 6,332,880 B1 | | 12/2001 | Yang et al. | WO | WO 95/34259 | 12/1995 |
| 6,355,032 B1 | | 3/2002 | Hovda et al. | WO | WO 96/11638 | 4/1996 |
| 6,416,508 B1 | | 7/2002 | Eggers et al. | WO | WO 96/32051 | 10/1996 |
| 6,428,512 B1 | * | 8/2002 | Anderson et al. ...... 604/170.01 | WO | WO 96/32885 | 10/1996 |
| 6,440,127 B1 | | 8/2002 | McGovern et al. | WO | WO 96/34559 | 11/1996 |
| 6,440,129 B1 | | 8/2002 | Simpson | WO | WO 96/34568 A | 11/1996 |
| 2001/0031963 A1 | | 10/2001 | Sharkey et al. | WO | WO 96/34571 | 11/1996 |
| 2001/0056278 A1 | | 12/2001 | Nield et al. | WO | WO 96/39914 | 12/1996 |
| 2002/0022830 A1 | | 2/2002 | Sharkey et al. | WO | WO 97/06855 | 2/1997 |
| 2002/0065541 A1 | | 5/2002 | Fredricks et al. | WO | WO 98/07468 | 2/1998 |
| 2002/0120259 A1 | | 8/2002 | Lettice et al. | WO | WO 98/11944 | 3/1998 |
| 2002/0188290 A1 | | 12/2002 | Sharkey et al. | WO | 98/17190 | 4/1998 |
| | | | | WO | WO 99/18878 | 4/1999 |

FOREIGN PATENT DOCUMENTS

| | | | |
|---|---|---|---|
| EP | 0 542 412 A1 | 5/1993 | |

WO    WO 99/47058    9/1999

\* cited by examiner

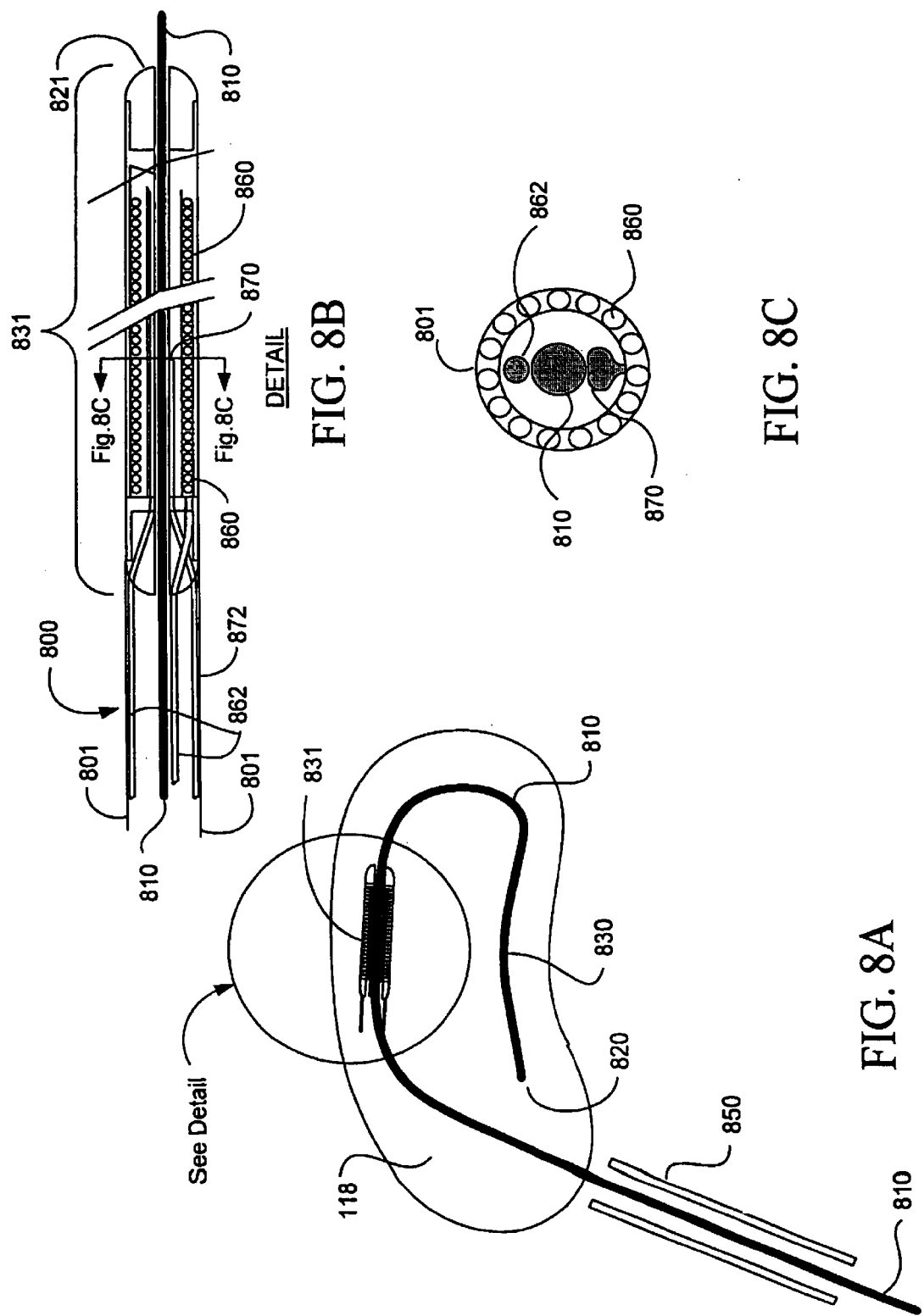

APPARATUS AND METHOD FOR ACCESSING AND PERFORMING A FUNCTION WITHIN AN INTERVERTEBRAL DISC

CROSS REFERENCE TO RELATED APPLICATIONS

This application claims the priority of U.S. Provisional Application No. 60/185,221 filed on Feb. 25, 2000, entitled "Apparatus And Method For Accessing And Performing A Function Within An Intervertebral Disc." The above application is hereby incorporated herein by reference.

BACKGROUND OF THE INVENTION

1. Field of the Invention

This invention relates to methods and apparatuses for modifying intervertebral disc tissue and more particularly to the treatment of annular fissures and disc defects using percutaneous techniques to avoid major surgical intervention.

2. Description of Related Art

Intervertebral disc abnormalities have a high incidence in the population and may result in pain and discomfort if they impinge on or irritate nerves. Disc abnormalities may be the result of trauma, repetitive use, metabolic disorders and the aging process and include such disorders but are not limited to degenerative discs (I) localized tears or fissures in the annulus fibrosus, (ii) localized disc herniations with contained or escaped extrusions, and (iii) chronic, circumferential bulging discs.

Disc fissures occur rather easily after structural degeneration of fibrous components of the annulus fibrosus during a part of the normal aging process that may be accelerated by trauma. Sneezing, bending or just attrition can tear these degenerated annulus fibrosus fibers, creating a fissure. The fissure may or may not be accompanied by extrusion of nucleus pulposus material into or beyond the annulus fibrosus. The fissure itself may be the sole morphological change, above and beyond generalized degenerative changes in the connective tissue of the disc. Even if there is no visible extrusion, biochemicals within the disc may leak out of the contained intervertebral disk and irritate surrounding structures. Disc fissures can also be debilitatingly painful. Initial treatment is symptomatic, including bed rest, pain killers and muscle relaxants. More recently, spinal fusion with cages have been performed when conservative treatment did not relieve the pain. The fissure may also be associated with a herniation of that portion of the annulus.

With a contained disc herniation, there are no free nucleus fragments in the spinal canal. Nevertheless, even a contained disc herniation is problematic because the outward protrusion can press on the spinal nerves or irritate other structures such as the corresponding nerve root. In addition to nerve root compression, escaped nucleus pulposus contents may chemically irritate neural structures. Current treatment methods include reduction of pressure on the annulus by removing some of the interior nucleus pulposus material by percutaneous nuclectomy. However, complications include disc space infection, nerve root injury, hematoma formation, instability of the adjacent vertebrae and collapse of the disc from a decrease in height.

Another disc problem occurs when the disc bulges outward circumferentially in all directions and not just in one location. Overtime, the disc weakens and takes on a "roll" shape or circumferential bulge. Mechanical stiffness of the joint is reduced and the joint and spinal column may become unstable. One vertebrae may settle on top of another. This problem continues as the body ages and accounts for a shortened stature in old age. With the increasing life expectancy of the population, such degenerative disc disease and impairment of nerve function are becoming major public health problems. As the disc "roll" extends beyond the normal circumference, the disc height may be compromised, foramina with nerve roots becomes compressed. In addition, osteophytes may form on the outer surface of the disc roll and further encroach on the spinal canal and foramina through which nerves pass. This condition is called lumbar spondylosis.

It has been thought that such disc degeneration creates segmental instability which disturbs sensitive structures which in turn register pain. Traditional, conservative methods of treatment include bed rest, pain medication, physical therapy or steroidal injections. Upon failure of conservative therapy, spinal pain (assumed to be due to instability) has been treated by spinal fusion, with or without instrumentation, which causes the vertebrae above and below the disc to grow solidly together and form a single, solid piece of bone. The procedure is carried out with or without discectomy. Other treatments include discectomy alone or disc decompression with or without fusion. Nuclectomy can be performed by removing some of the nucleus to reduce pressure on the annulus. However, complications include disc space infection, nerve root injury, hematoma formation, and instability of adjacent vertebrae.

These interventions have been problematic in that alleviation of back pain is unpredictable even if surgery appears successful. In attempts to overcome these difficulties, new fixation devices have been introduced into the market, including but not limited to pedicle screws and interbody fusion cages. Although pedicle screws provide a high fusion success rate, there is still no direct correlation between fusion success and patient improvement in function and pain. Studies on fusion have demonstrated success rates of between 50% and 67% for pain improvement, and a significant number of patients have more pain postoperatively. Therefore, different methods of helping patients with degenerative disc problems need to be explored.

FIGS. 1A and 1B illustrate a cross-sectional anatomical view of a vertebra and associated disc and a lateral view of a portion of a lumbar and thoracic spine, respectively.

Structures of a typical cervical vertebra (superior aspect) are shown in FIG. 1A: 104—lamina; 106—spinal cord; 108—dorsal root of the spinal nerve; 114—ventral root of the spinal nerve; 116—posterior longitudinal ligament; 118—intervertebral disc; 120—nucleus pulposus; 122—annulus fibrosus; 123—anterior longitudinal ligament; 126—vertebral body; 128—pedicle; 130—vertebral artery; 132—vertebral veins; 134—superior articular facet; 136—posterior lateral portion of the annulus; 138—posterior medial portion of the annulus; and 149—spinous process. In FIG. 1A, one side of the intervertebral disc 118 is not shown so that the anterior vertebral body 126 can be seen. FIG. 1B is a lateral aspect of the lower portion of a typical spinal column showing the entire lumbar region and part of the thoracic region and displaying the following structures: 118—intervertebral disc; 126—vertebral body; 142—spinous process; 170—inferior vertebral notch; 110—spinal nerve; 174—superior articular process; 176—lumbar curvature; and 180—sacrum.

The presence of the spinal cord and the posterior portion of the vertebral body, including the spinous process, and superior and inferior articular processes, prohibit introduction of a needle or trocar from a directly posterior position. This is important because the posterior disc wall is the site of symptomatic annulus tears and disc protrusions/extrusions that compress or irritate spinal nerves for most degenerative disc syndromes. The inferior articular process along with the pedicle and the lumbar spinal nerve, form a small "triangular" window through which introduction can be achieved from a posterior lateral approach. FIG. 1D is an overhead view of an instrument introduced by the posterior lateral approach. It is well known to those skilled in the art that percutaneous access to the disc is achieved by placing an introducer into the disc from this posterior lateral approach, but the triangular window does not allow much room to maneuver. Once the introducer pierces the tough annulus fibrosus, the introducer is fixed at two points along its length and has very little freedom of movement. Thus, this approach has allowed access only to small central and anterior portion of the nucleus pulposus. Current methods do not permit percutaneous access to the posterior half of the nucleus or to the posterior wall of the disc. Major and potentially dangerous surgery is required to access these areas.

Accordingly, these problems with spinal column surgery have been addressed by Applicants in U.S. Pat. Nos. 5,980,504, 6,007,570, U.S. application Ser. No. 09/363,824, filed Jul. 30, 1999, U.S. application Ser. No. 09/236,816 filed Jan. 25, 1999, U.S. application Ser. No. 09/162,704 filed Sep. 29, 1998, U.S. application Ser. No. 09/153,552 filed Sep. 15, 1998 and U.S. application Ser. Nos. 08/881,525, 08/881,692, 08/881,694, all filed Jun. 24, 1997, which are incorporated by reference Accordingly, it is desirable to provide an improved access apparatus and method by which the interior nucleus of an intervertebral disc may be accessed and annular fissures or herniations can be treated or repaired. It would be further desirable to provide a modular exchange system to address various functions such as delivery of energy, delivery of medicaments, removal of material or providing access for physical and chemical modification of the nucleus and annulus.

SUMMARY OF THE INVENTION

The present invention provides novel apparatus and methods for accessing intervertebral disc, as well as diagnosing and treating intervertebral disc disorders. In one embodiment, an apparatus is provided for accessing a selected section of an intervertebral disc. The apparatus comprises a catheter having a lumen; and a guide wire having a distal portion and a proximal portion, and configured to be positioned within and moved relative to the lumen of the catheter; wherein the guide wire is capable of navigating itself within an intradiscal section of the intervertebral disc adjacent an inner wall of an annulus of the disc to the selected section of the disc and the catheter is capable of being advanced relative to the guide wire such that the catheter follows a path of the guide wire within the intradiscal section of the disc adjacent the inner wall of the annulus of the disc to the selected section.

According to this embodiment, the guide wire is built to possess (a) sufficient rigidity to be advanceable through a nucleus pulposus and around the inner wall of an annulus fibrosus under a force applied longitudinally to the proximal end of the core wire, (b) insufficient penetration ability to be advanceable out through the annulus fibrosus under the applied force, and (c) sufficient flexibility in a direction of a disc plane to be compliant with the inner wall.

Also according to this embodiment, the distal portion of the guide wire includes a spring coil to adjust flexibility of the guide wire. A forming ribbon may be incorporated in the distal portion of the guide wire to support the spring coil. The spring coil may be fully coated with Teflon or other biocompatible materials. The distal portion of the guide wire may be tapered to a smaller diameter toward the distal end.

Still according to this embodiment, the distal portion of the guide wire has a distal tip at the extremity of the distal portion of the guide wire. The distal portion of the guide wire may have one or more flat sides. The distal tip may be configured to be non-piercing through an annulus fibrosus, for example, including a blunt tip or a rolling ball tip. The distal tip may also include a locking mechanism for securing the guide wire within the selected section of the intervertebral disc, such as within an intradiscal section of the disc adjacent an inner wall of an annulus of the disc. The locking mechanism may include a retractable hook or a plurality of directional hooks. Alternatively, the guide wire may be capable of cross-locking itself once the guide wire is advanced to the selected section of the disc.

Still according to this embodiment, the proximal portion of the guide wire may preferably have an outer diameter between about 0.005–0.025 inches. The distal portion of the guide wire may preferably have an outer diameter between about 0.002–0.012 inches. The proximal portion of the guide wire may preferably be between about 10–15 inches long. The distal portion of the guide wire may preferably be between about 0.2–1.2 inches long. The distal portion of the guide wire may preferably have a length at least one-half of a diameter of the nucleus pulposus.

The apparatus of the present invention may further include a dialator sheath configured to be slid or passed over the guide wire for introducing the catheter onto the guide wire.

The guide wire of the apparatus may be actively steerable. At least a portion of guide wire may be radiographically visible.

The guide wire of the apparatus may have a bending stiffness as measured in Taber stiffness units preferably between about 2–400 and more preferably about 3–150 units in a desired bending plane. The distal portion of the guide wire may have a column strength preferably between about 0.2–7 kg, and more preferably between about 0.7–4 kg.

The catheter of the apparatus may further include a functional element for performing a function adjacent the selected section, such as delivering energy, adding material and removing material. In one aspect, the functional element may also be an irrigation lumen extending from a proximal end of the catheter to the intradiscal section. In another aspect, the functional element may comprise a thermal energy delivery device. A thermal energy source may be operably attached to the thermal energy delivery device through the catheter. Examples of the thermal energy delivery devices include, but are not limited to, microwave probes, optical fibers, radio frequency electrodes, thermal resistive heaters, integrated circuits and ultrasound emitters.

The functional element may be capable of delivering a controlled amount of energy at or near the fissure such that no vaporization occurs at or near the fissure when energy is delivered by the functional element. Optionally, the functional element may be capable of delivering a controlled amount of energy at or near the fissure such that no material other than water is removed at or near the fissure when energy is delivered by the functional element. Also optionally, the functional element may be capable of delivering a controlled amount of energy at or near the fissure such that no destructive lesion is formed on a disc at or near the fissure when energy is delivered by the functional element.

The catheter of the apparatus may further comprise at least one sensor capable of monitoring temperature, power, voltage or a combination thereof and the input from the sensor controls energy supplied to the thermal energy device.

In another embodiment of the present invention, a method of treating an intervertebral disc is provided. The method comprises: causing a guide wire to navigate itself within an intradiscal section of the intervertebral disc adjacent an inner wall of an annulus of the disc to a selected section of the disc; taking a catheter which has the guide wire positioned within a lumen of the catheter; and advancing the catheter relative to the guide wire such that the catheter follows a path of the guide wire within the intradiscal section of the disc adjacent the inner wall of the annulus of the disc to the selected section.

According to this embodiment, causing the guide wire to navigate itself may include applying a longitudinal force to the guide wire which is sufficient to advance the guide wire through the nucleus pulposus and around the inner wall of an annulus fibrosus, but which force is insufficient for the guide wire to puncture the annulus fibrosus.

Also according to this embodiment, the selected section of the disc may be a posterior medial, posterior lateral, anterior lateral, or anterior medial section of the annulus fibrosus, or a combination thereof.

Still according to this embodiment, the method may further include performing a function adjacent the selected section by using a catheter that includes a functional element for performing the function. The function may be delivering energy, adding material and removing material. For example, the functional element may be a heating element coupled with a temperature sensor. Such a heating element may be a coil heating element, a flat heating element, or a flex ribbon heating element. Alternatively, the guide wire itself may include a heating element.

The method according to the present invention may further include using the function to treat annular fissures, for example, by adding sufficient energy to the selected section of the disc. The sufficient energy may be added to shrink the collagen component of the annulus fibrosus around the fissure or to cauterize granulation tissue in the fissure.

Alternatively, the functional element may be a lumen capable of delivering or aspirating material. Accordingly, the method may further include placing a material in the disc. Such a material may be electrolyte solutions, contrast media, pharmaceutical agents, chemonucleolytic enzymes, hydrogel, osteoinductive substances, chondrocyte-inductive substances, sealants, collagen, fibrinogen and thrombin, and any combination thereof.

Accordingly, an advantage of the invention is to provide a simple and maneuverable apparatus for accessing the interior of an intervertebral disc. The apparatus should be able to advance and navigate through the nucleus pulposus and along the annulus fibrosus to provide access to the site of the annular fissure.

Still a further advantage of the invention is to provide a device which has a distal end that is inserted into the disc and access the posterior, posterior lateral and posterior medial regions of the inner wall of the annulus fibrosus.

Another advantage of the invention is to provide an apparatus and method which is exchangeable over the access portion of the invention to provide various functions within the intervertebral disc such as diagnostic viewing, energy delivery, mechanical manipulation, removal or addition of material, delivery of medicament and pain management. The construction of the separate guide wire and catheter is advantageous in that both structural units may be designed separately without relying on a single structure for both support and treatment.

The accompanying drawings, which are incorporated in and form a part of this specification, illustrate embodiments of the invention and, together with the description, serve to explain the principles of the invention.

BRIEF DESCRIPTION OF THE FIGURES

FIG. 8A is an illustration of the guide wire and introducer according to the present invention with a section of the distal portion of the treatment catheter being extended over the guide wire.

FIG. 8B is a detailed longitudinal cross-sectional view of the distal portion treatment catheter of FIG. 8A over the guide wire having a heating element and a temperature sensor.

FIG. 8C is a cross-sectional view of the distal portion of the treatment catheter of FIG. 8B showing the guide wire placement within the catheter.

DETAILED DESCRIPTION OF SPECIFIC EMBODIMENTS

Figure 1A:
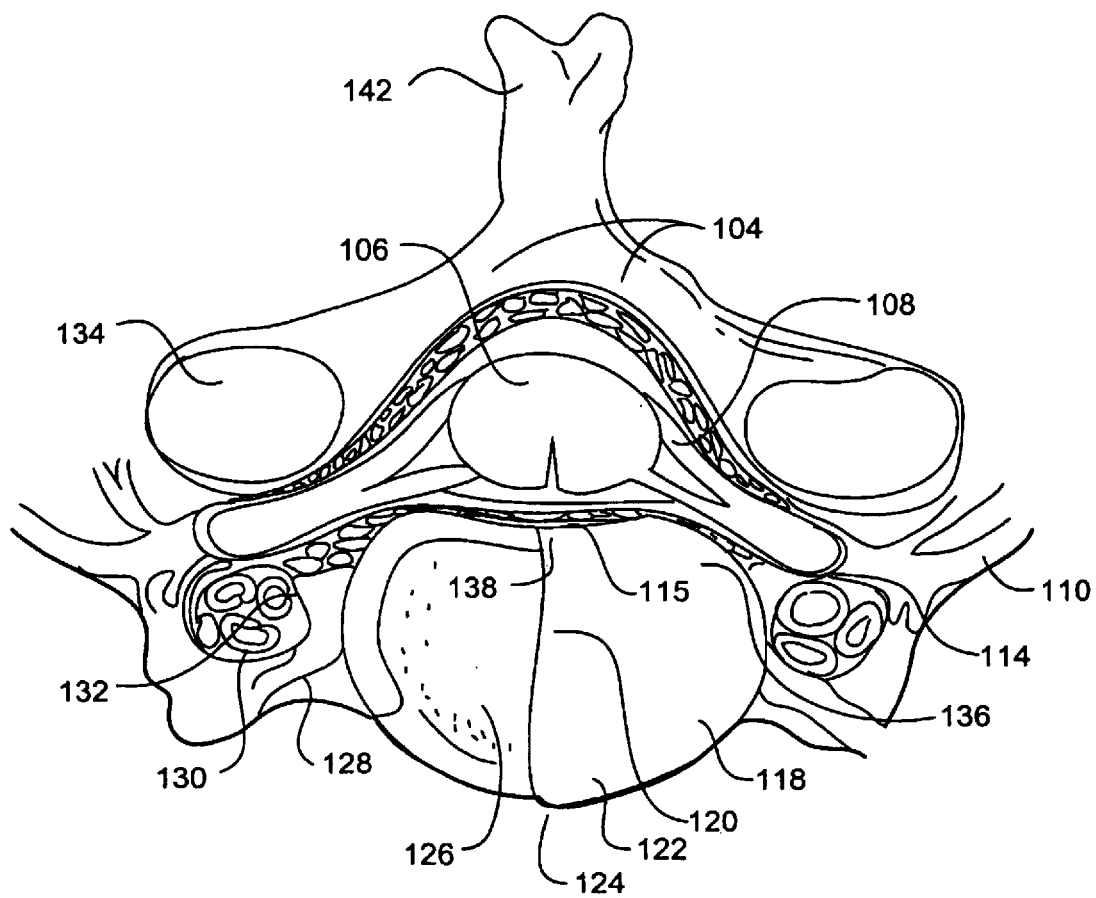
FIG. 1A is a superior cross-sectional anatomical view of a cervical disc and associated vertebral structure.
Figure 1B:
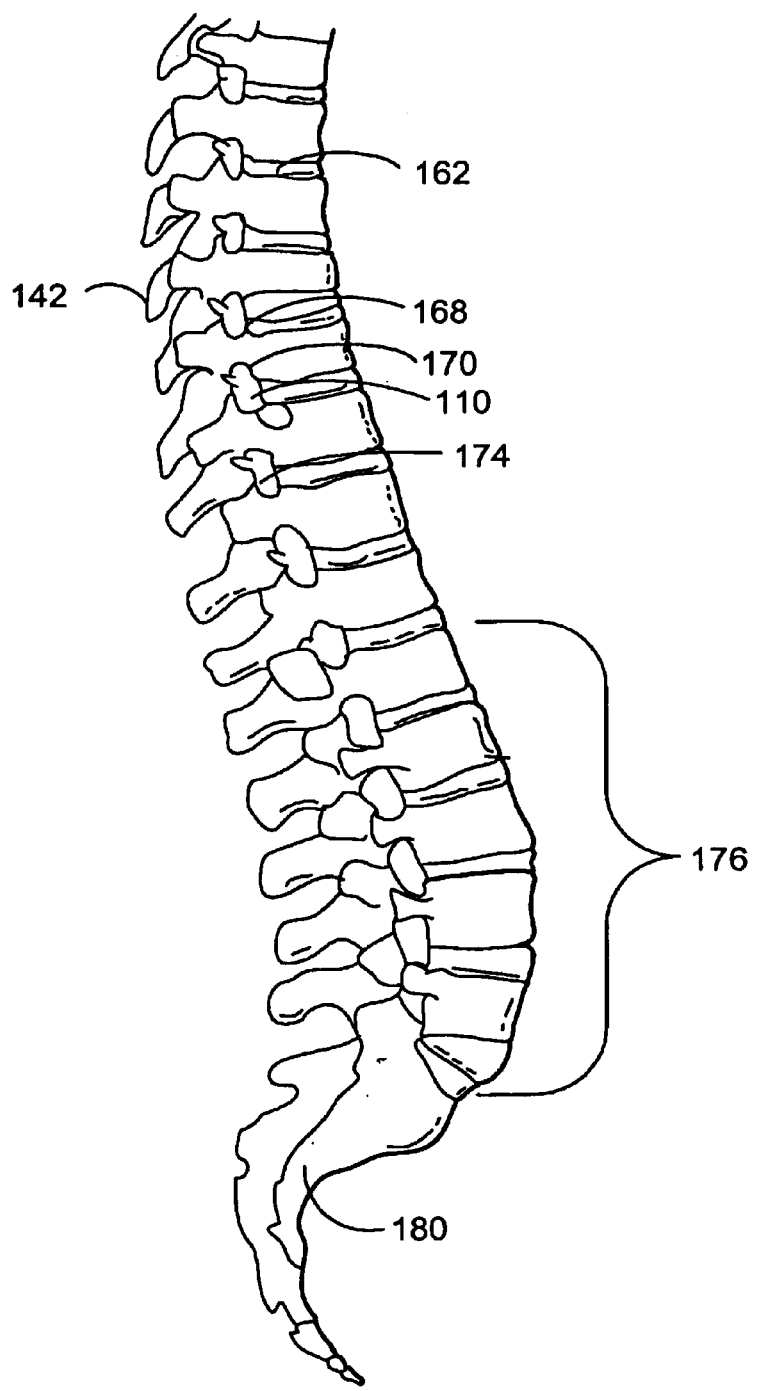
FIG. 1B is a lateral anatomical view of a portion of a lumbar spine.
Figure 1D:
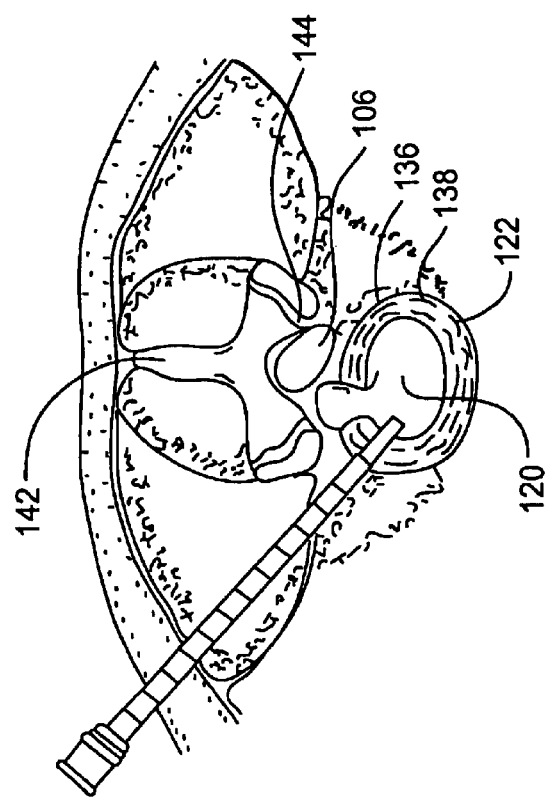
FIG. 1D is a superior cross-sectional view of a specified posterior lateral approach into a herniated intervertebral disc.
Figure 1C:
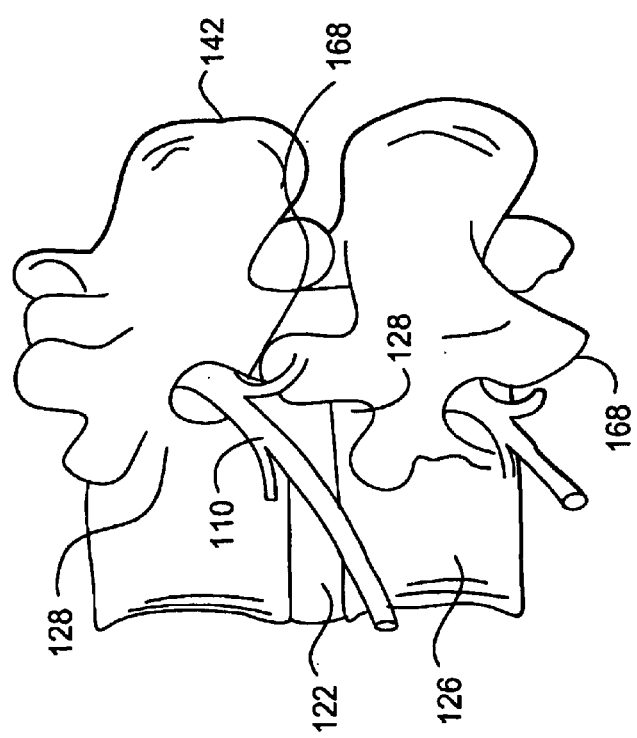
FIG. 1C is a posterior-lateral anatomical view of two adjacent lumbar vertebrae.

The present invention provides novel apparatus and methods for accessing and performing functions within an intervertebral disc, particularly for treating intervertebral disc disorders such as sealing fissures of the annulus fibrosus, which may or may not be accompanied with contained or escaped extrusions. The present invention may also involve the removal or addition of material to the intervertebral disc.

In one embodiment, an apparatus is provided for accessing a selected section of an intervertebral disc. The apparatus comprises a catheter having a lumen; and a guide wire having a distal portion and a proximal portion, and configured to be positioned within and moved relative to the lumen of the catheter; wherein the guide wire is capable of navigating itself within an intradiscal section of the intervertebral disc adjacent and/or through an inner wall of an annulus of the disc to the selected section of the disc and the catheter is capable of being advanced relative to the guide wire such that the catheter follows a path of the guide wire within the intradiscal section of the disc to the selected section.

According to this embodiment, the guide wire is built to possess (a) sufficient rigidity to be advanceable through a nucleus pulposus and through and/or around the inner wall of an annulus fibrosus under a force applied longitudinally to the proximal end of the core wire, (b) insufficient penetration ability to be advanceable out through the annulus fibrosus under the applied force, and (c) sufficient flexibility in a direction of a disc plane to be compliant with the inner wall.

Also according to this embodiment, the distal portion of the guide wire includes a spring coil to adjust flexibility of the guide wire. A forming ribbon may be incorporated in the distal portion of the guide wire to support the spring coil. The spring coil may be fully coated with Teflon or other biocompatible materials. The distal portion of the guide wire may be tapered to a smaller diameter toward the distal end.

Still according to this embodiment, the distal portion of the guide wire has a distal tip at the extremity of the distal portion of the guide wire. The distal portion of the guide wire may have one or more flat sides. The distal tip may be configured to be non-piercing through an annulus fibrosus, for example, including a blunt tip or a rolling ball tip. The distal tip may also include a locking mechanism for securing the guide wire within the selected section of the intervertebral disc, such as within an intradiscal section of the disc adjacent an inner wall of an annulus of the disc. The locking mechanism may include a retractable hook or a plurality of directional hooks. Alternatively, the guide wire may be capable of cross-locking itself once the guide wire is advanced to the selected section of the disc.

Still according to this embodiment, the proximal portion of the guide wire may preferably have an outer diameter between about 0.005–0.025 inches. The distal portion of the guide wire may preferably have an outer diameter between about 0.002–0.012 inches. The proximal portion of the guide wire may preferably be between about 10–15 inch long. The distal portion of the guide wire may preferably be between about 0.2–1.2 inch long. The distal portion of the guide wire may preferably have a length at least one-half of a diameter of the nucleus pulposus.

The apparatus of the present invention may further include a dialator sheath configured to be slid or passed over the guide wire for introducing the catheter onto the guide wire.

The guide wire of the apparatus may be actively steerable. At least a portion of guide wire may be radiographically visible.

The guide wire of the apparatus may have a bending stiffness as measured in Taber stiffness units preferably between about 2–400 and more preferably about 3–150 units in a desired bending plane. The distal portion of the guide wire may have a column strength preferably between about 0.2–7 kg, and more preferably between about 0.7–4 kg.

The catheter of the apparatus may further include a functional element for performing a function adjacent the selected section, such as delivering energy, adding material and removing material. In one aspect, the functional element may also be an irrigation lumen extending from a proximal end of the catheter to the intradiscal section. In another aspect, the functional element may comprise a thermal energy delivery device. A thermal energy source may be operably attached to the thermal energy delivery device through the catheter. Examples of the thermal energy delivery devices include, but are not limited to, microwave probes, optical fibers, radio frequency electrodes, plasma and/or ion generators, and ultrasound emitters.

The functional element may be capable of delivering a controlled amount of energy at or near the fissure such that no vaporization occurs at or near the fissure when energy is delivered by the functional element. Optionally, the functional element may be capable of delivering a controlled amount of energy at or near the fissure such that no material other than water is removed at or near the fissure when energy is delivered by the functional element. Also optionally, the functional element may be capable of delivering a controlled amount of energy at or near the fissure such that no destructive lesion is formed on a disc at or near the fissure when energy is delivered by the functional element.

The catheter of the apparatus may further comprise at least one sensor capable of monitoring temperature, power, voltage or a combination thereof and the input from the sensor controls energy supplied to the thermal energy device.

For example, an apparatus of the present invention is in the form of an externally guidable guide wire and a catheter with a lumen for accessing and modifying the intradiscal structure and environment within or a selected location of an intervertebral disc having a nucleus pulposus and an annulus fibrosus, the annulus having an inner wall. Use of various exchange-type catheters for different functions provides a variable and highly modifiable treatment system for delivering energy, adding or removing material from the intervertebral disc. For ease of reference to various manipulations and distances described below, the nucleus pulposus can be considered as having a given diameter in a disc plane between opposing sections of the inner wall. This nucleus pulposus diameter measurement allows instrument sizes (and components of instruments) designed for one size disc to be readily converted to sizes suitable for an instrument designed for a different size of disc such as the difference between cervical and lumbar discs.

The operational portions of the apparatus of the present invention are guided to a location in or near the annular fissure in the annulus of the intervertebral disc using techniques and apparatuses typical of percutaneous interventions. For convenience and to indicate that the apparatus of the invention can be used with any insertional apparatus that provides access and proximity to the intervertebral disc, including many such insertional apparatuses known in the art, the term "introducer" is used to describe this aid to the apparatus and method. An introducer has an internal introducer lumen with a distal opening at a terminus of the introducer to allow insertion and subsequent manipulation of the operational portions of the apparatus through the body into and within the interior of a disc.

In another embodiment of the present invention, a method of treating an intervertebral disc is provided. The method comprises: causing a guide wire to navigate itself within an intradiscal section of the intervertebral disc adjacent an inner wall of an annulus of the disc to a selected section of the disc; taking a catheter which has the guide wire positioned within a lumen of the catheter; and advancing the catheter relative to the guide wire such that the catheter follows a path of the guide wire within the intradiscal section of the disc adjacent the inner wall of the annulus of the disc to the selected section.

According to this embodiment, causing the guide wire to navigate itself may include applying a longitudinal force to the guide wire which is sufficient to advance the guide wire through the nucleus pulposus and through and/or around the inner wall of an annulus fibrosus, but which force is insufficient for the guide wire to puncture the annulus fibrosus.

Also according to this embodiment, the selected section of the disc may be a posterior medial, posterior lateral, anterior lateral, or anterior medial section of the annulus fibrosus, or a combination thereof.

Still according to this embodiment, the method may further include performing a function adjacent the selected section by using a catheter that includes a functional element for performing the function. The function may be delivering energy, adding material and removing material. For example, the functional element may be a heating element coupled with a temperature sensor. Such a heating element may be a coil heating element, a flat heating element, or a flex ribbon heating element. Alternatively, the guide wire itself may include a heating element.

The method according to the present invention may further include using the function to treat an annular fissure, for example, by adding sufficient energy to the selected section of the disc. The sufficient energy may be added to shrink the collagen component of the annulus fibrosus around the fissure or to cauterize granulation tissue in the fissure and thus, stimulate a healing response by the body.

Alternatively, the functional element may be a lumen capable of delivering aspirating material. Accordingly, the method may further include placing a material in the disc. Such a material may be electrolyte solutions, contrast media, pharmaceutical agents, chemonucleolytic enzymes, hydrogel, osteoinductive substances, chondrocyte-inductive substances, sealants, collagen, fibrinogen and thrombin, and any combination thereof.

The method of the present invention which involves accessing the nucleus pulposus of an intervertebral disc is easily carried out with an apparatus according to the present invention.

In general, an introducer is provided that is located in a patient's body so that its proximal end is external to the body and the distal opening of its lumen is internal to the body and (1) internal to the annulus fibrosus or (2) adjacent to an annular opening leading to the nucleus pulposus, such as an annular tear or trocar puncture that communicates with the nucleus pulposus.

A guide wire is slid into position within and through the introducer lumen so that a distal tip of the guide wire is positioned at the selected location of the disc by advancing or retracing the guide wire in the introducer lumen and optionally twisting the proximal end of the guide wire to precisely navigate the guide wire. By carefully selecting rigid characteristics of the guide wire and with a flexible distal portion and blunt non-traumatic distal tip and by careful selection of the flexibility in one plane versus the orthogonal plane, the distal portion of the guide wire will curve along the inner wall of the annulus fibrosus as it is navigated and is selectively guided to an annular tear or fissure at selected locations within the intervertebral disc.

A treatment catheter with a lumen for at least the guide wire is positioned over the guide wire and slid over the guide wire and navigated to the distalmost portion of the guide wire within the disc. The treatment catheter is configured to provide a function selected from ablation or shrinkage, delivery of medicaments, suction, viewing or monitoring within the disc, ultrasound delivery for treatment, mechanical manipulation, and/or ionization of disc tissue.

The treatment catheter may also be "exchanged" such that various treatment modalities incorporated into separate catheters can be positioned and slid over the guide wire to provide various treatments without removal of the guide wire thereby providing less trauma to the patient. In addition, such exchangeability and versatility of the apparatus maximizes the variety of functions to be performed within the intradiscal section of the disc without potentially costly construction of various catheters each having a built-in guide wire.

The following descriptions of FIGS. 1 to 12 describe specific embodiments of the invention. The guide wire and treatment catheter of the present invention is illustrated but is not limited to this embodiment. The descriptive language used both in the specification and claims is for the purposes of clarity and convenience and not with any purpose or implied limitation to the surgical art or along a columnar vertebral structure as is typical in the spinal column.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Figure 2:
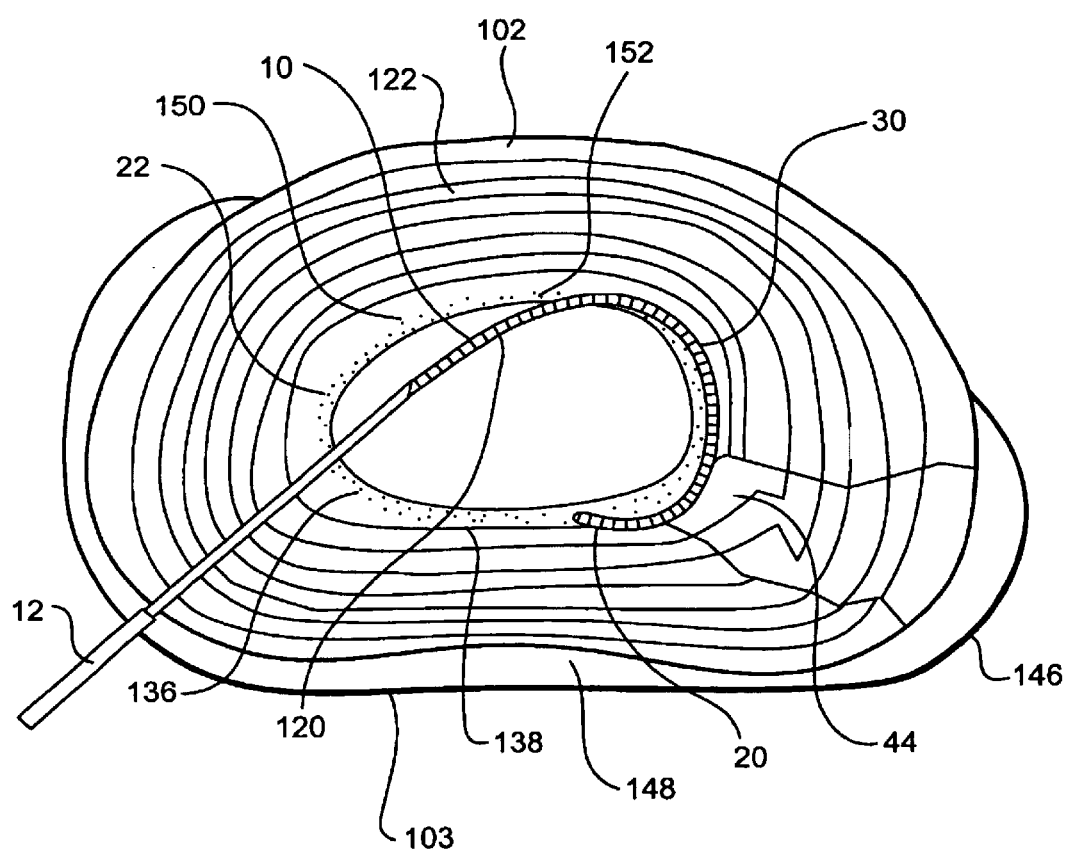
FIG. 2 is a cross-sectional view of an intervertebral disc with a portion of an intervertebral apparatus of the present invention inserted into an intervertebral disc with a fissure along a posterior aspect of the annulus fibrosus.

Referring now to FIG. 2, the anatomy of an intervertebral disc is illustrated with an apparatus according to the present invention inserted into the disc. Structures of the disc are identified and described by these anatomical designations: 136—posterior lateral inner annulus, 138—posterior medial inner annulus, 122—annulus fibrosus, 120—nucleus pulposus, 146—annulus/dural interface, 148—annulus/posterior longitudinal ligament interface, 150—anterior lateral inner annulus, and 152—anterior medial inner annulus. The method and treatment according to the present invention are approached from the posterior aspect 103 of the intervertebral disc towards the anterior aspect 102 of the disc.

FIG. 2 illustrates that the mechanical characteristics of flexible distal section 30 of guide wire 10 are selected to have (1) sufficient column strength along the longitudinal axis of the guide wire to be able to advance and push through the nucleus pulposus 120 and (2) different flexural strengths along two axes orthogonal to the longitudinal axis to allow controlled bending of the guide wire 10. These parameters make the guide wire easily conformable and guidable along or directly through inner wall 22 of the annulus fibrosus 122 to reach a desired location, such as the posterior wall along posterior medial annulus 138. Distal tip 20 of the guide wire 10 is preferably anti-traumatic such that the guide wire does not penetrate through the fissures or tears 44 in the annulus.

Figure 3:
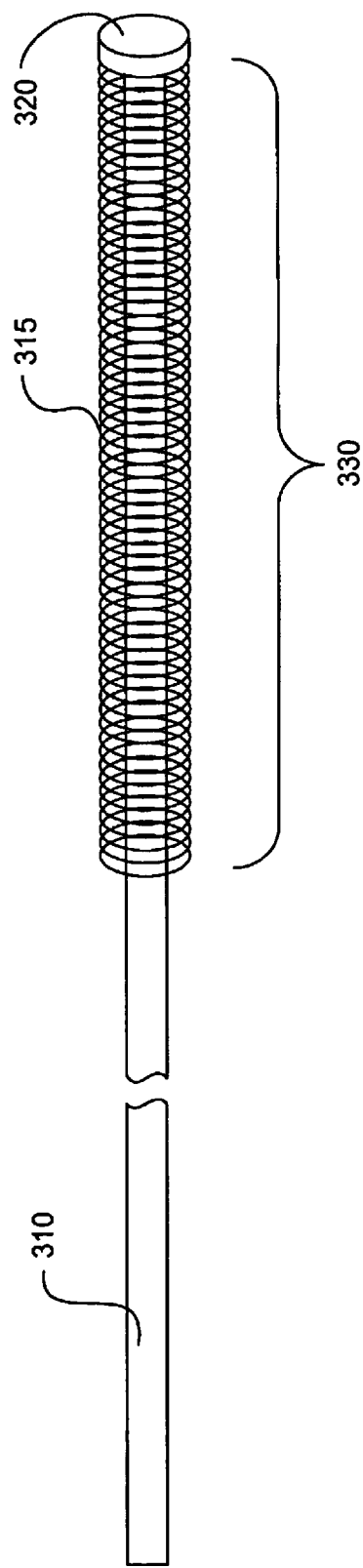
FIG. 3 is a plan view of a guide wire of the invention showing a central portion, a distal flexible section and a distal tip.

Guide wire 310 is illustrated in one embodiment in FIG. 3. The guide wire 310 consists of a core with a generally constant diameter from a proximal portion to a distal tip 320. A flexible distal portion 330 is located at or near the distal tip 320 of guide wire 310. A coil 315 is positioned at or near the distal tip such that a differential flexibility characteristic allows the guide wire to navigate through the nucleus pulposus of the disc.

Figure 4A:
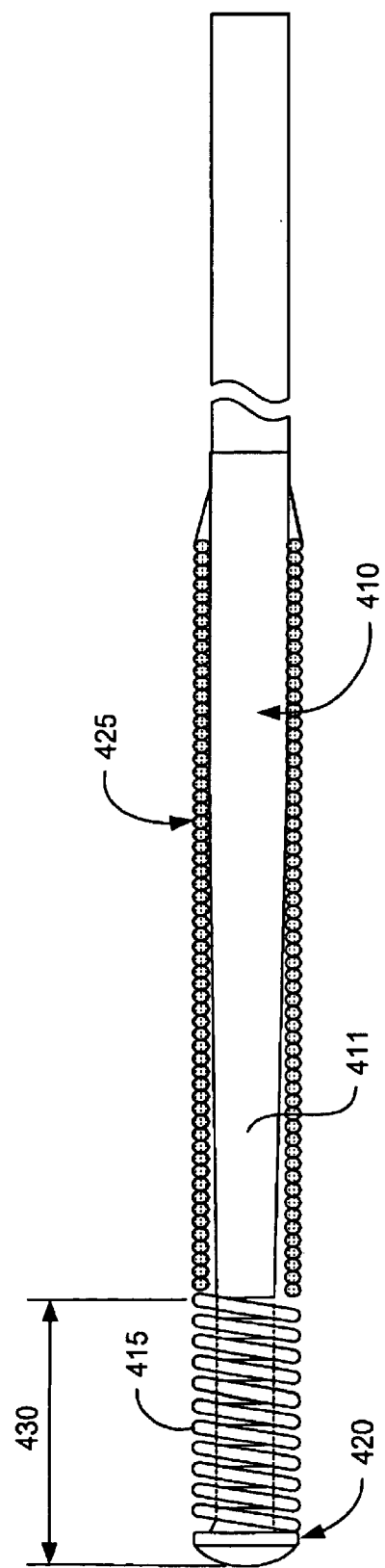
FIG. 4A is a cross-sectional view of the guide wire of the present invention including a specific embodiment of a tapered guide wire at the distal flexible section.

Referring to FIG. 4A, the guide wire 410 is configured with a tapering section 411 which provides a differential bending stiffness through the distal portion 425 of the guide wire. Flexible distal portion 430 includes a coil 415 which allows the tapering section 415 to curve and to navigate along the wall of the annulus. Blunt distal tip 420 limits and prevents the distal tip from penetrating large fissures in the annulus fibrosus.

Figure 4B:
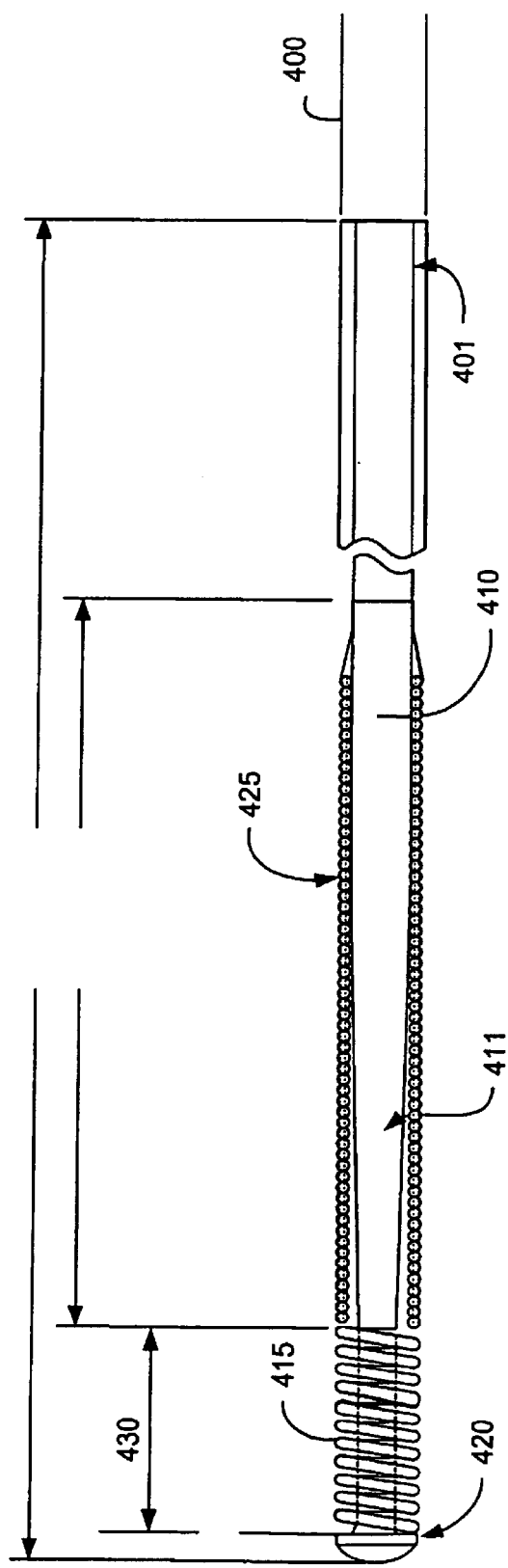
FIG. 4B is a cross-sectional view of the guide wire of FIG. 4A with a treatment catheter positioned proximally over the guide wire.

In FIG. 4B, the catheter 400 is shown with a lumen 401 which is large enough to pass over the guide wire 410. The catheter 400 is sized to pass over the distal portion 425 and flexible distal portion 430 and distal tip 420. It is preferable that the catheter 400 have a larger diameter than the entire core guide wire 410 such that the distal end of the catheter may extend beyond the placement of the distal end 420 of guide wire 410.

Figure 4C:
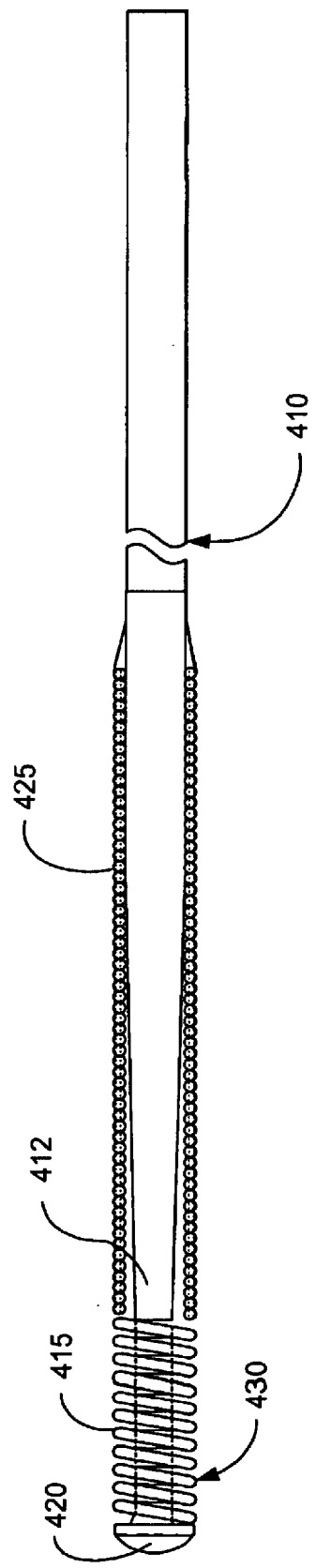
FIG. 4C is a cross-sectional view of a specific embodiment of the guide wire of the present invention with a ribbon-shaped core section at the distal flexible section.

FIG. 4C is another specific embodiment of the guide wire 410 wherein the distal tip portion 425 has flat core 412 at the distal end through flexible distal portion 430. The flattened ribbon configuration of flat core 412 allows the coils around distal tip 415 to have even greater flexibility when navigating through the nucleus of the intervertebral disc. The distal tip 420 is a blunt tip to provide an anti-penetration characteristic. In will be appreciated that distal tip 420 may be configured as a ball which is soldered to the flat core 412 for protection and steerability of the core wire 410.

Figure 5A:
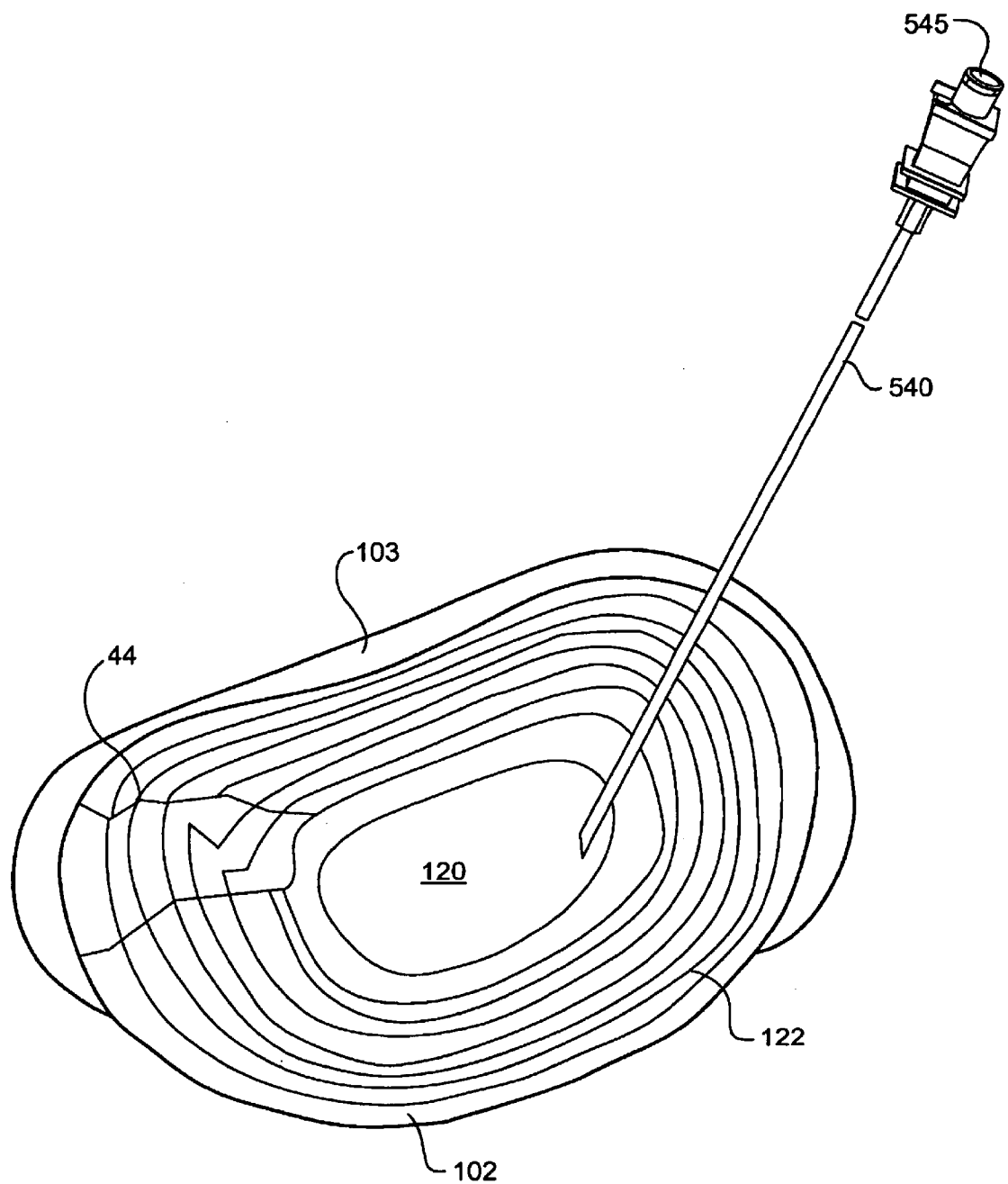
FIG. 5A illustrates a partial cross-sectional view of the intervertebral disc with an introducer inserted into the disc.

Referring now to FIG. 5A, the intervertebral disc is illustrated with a posterior aspect 103 and an anterior aspect 102. The introducer 540 is inserted through the body into the nucleus pulposus 120 of the disc. The introducer needle has a hub 545 which is located outside of the patient's body to receive and guide the core wire. The introducer is preferably not inserted into the annulus fibrosus 122 but can be positioned either away from the fissures or tear 44 or on the same posterior aspect (not shown).

Figure 5B:
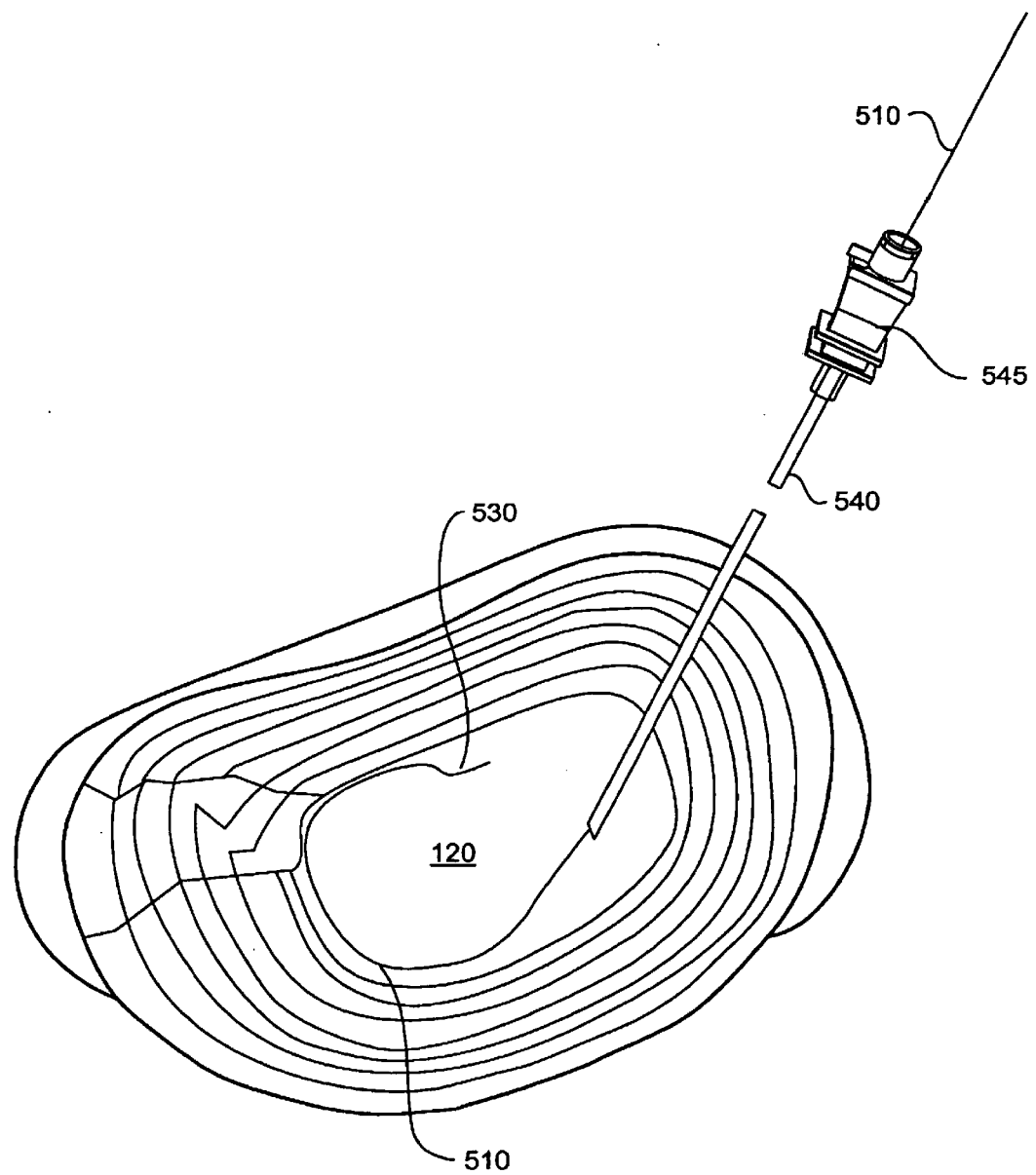
FIG. 5B is a partial cross-sectional view of the guide wire of the present invention inserted through the introducer of FIG. 5A and navigated and positioned along a specified posterior aspect of the intervertebral disc.

FIG. 5B demonstrates the guide wire 510 inserted through the hub 545 and introducer 540 through the body to the nucleus pulposus 120. The guide wire 510 has sufficient rigidity and torsional characteristics such that the guide wire is advanced through the introducer 540 and navigates along or through the inner wall of the annulus fibrosus. The distal portion 530 of the guide wire is then positioned along the annular fissure or tear before treatment.

Figure 5C:
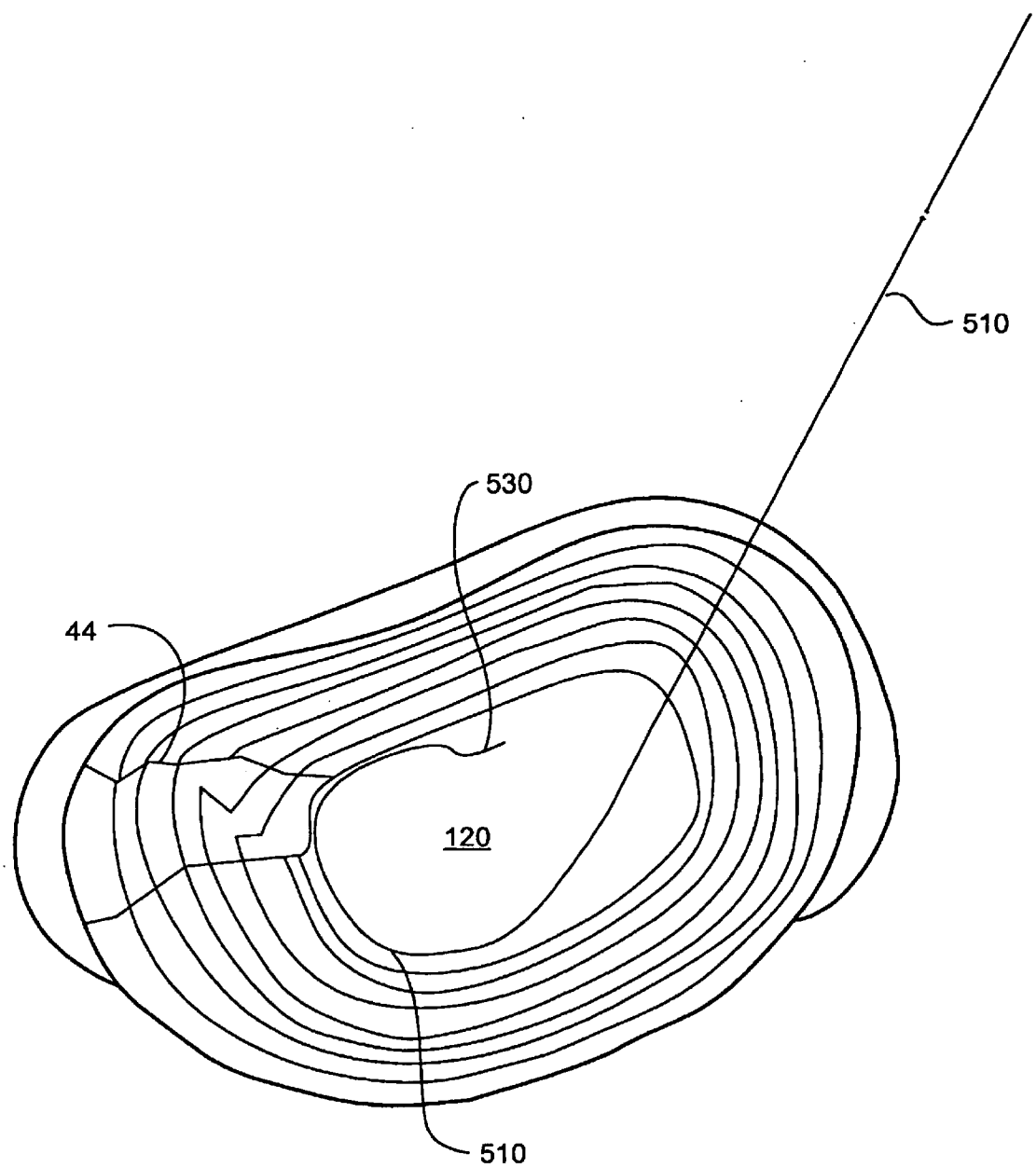
FIG. 5C is a cross-sectional view of the core wire of FIG. 5B remaining in place at after the introducer is removed.

FIG. 5C illustrates the guide wire 510 remaining in place after the introducer is removed, thus leaving no sharpened structures along the path of the guide wire. The distal portion 530 remains placed along the posterior inner wall of the annulus near the tear.

Figure 5D:
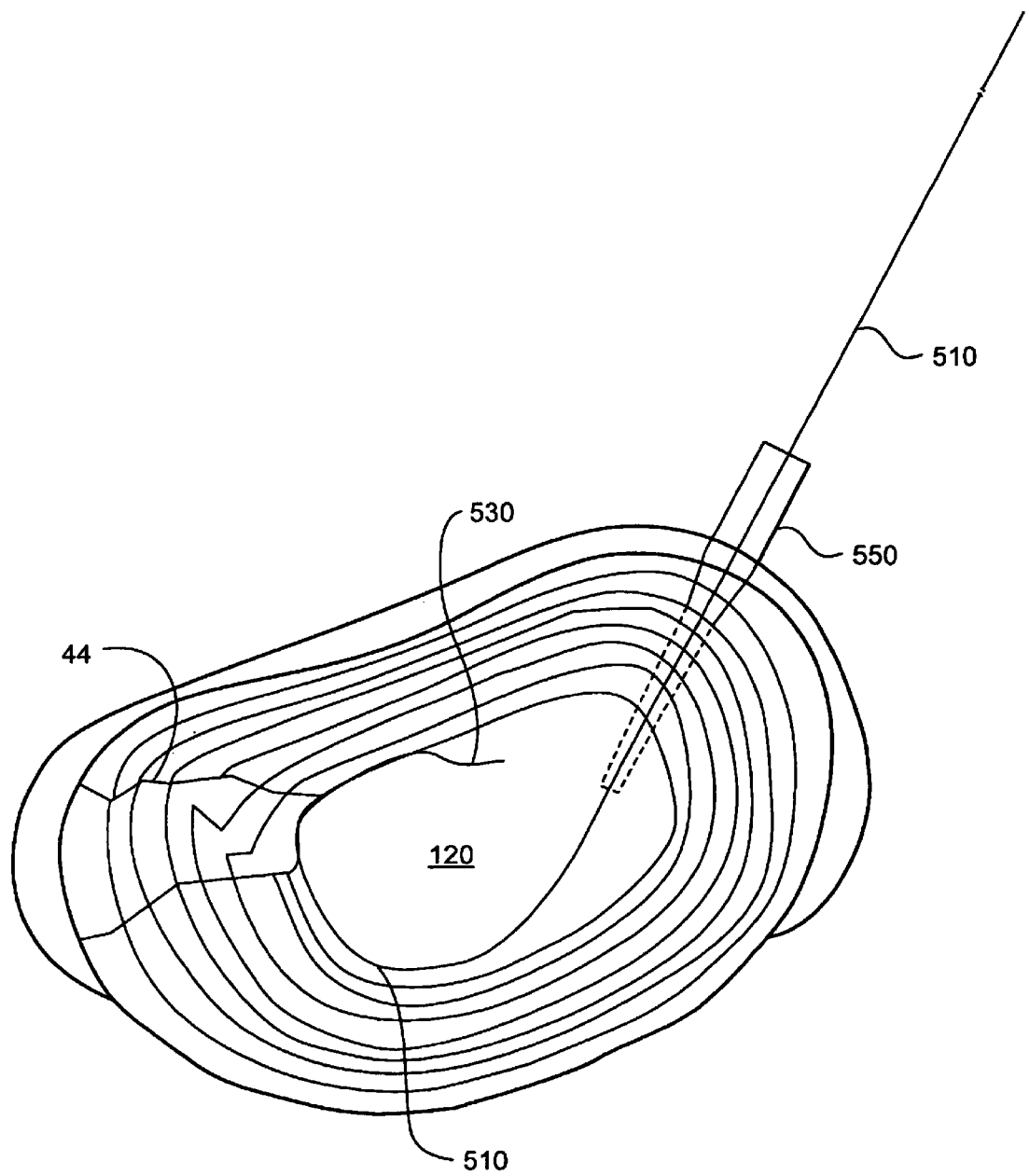
FIG. 5D is a cross-sectional view of the guide wire of FIG. 5B with a dialator sheath inserted into the intervertebral disc over the guide wire.

Referring to FIG. 5D, a dialator sheath 550 is inserted over the guide wire 510. Sheath 550 performs a similar function as a guiding catheter which is known in the art. The sheath supports the catheter (not shown) and guide wire when the catheter is advanced through the body percutaneously and also protects the catheter from any collateral damage that may be associated when the catheter is inserted over the guide wire. Sheath 550 also provides a conduit for the catheter into the nucleus in the event that the catheter would encounter some resistance which could damage the treatment modalities associated with the catheter.

Figure 5E:
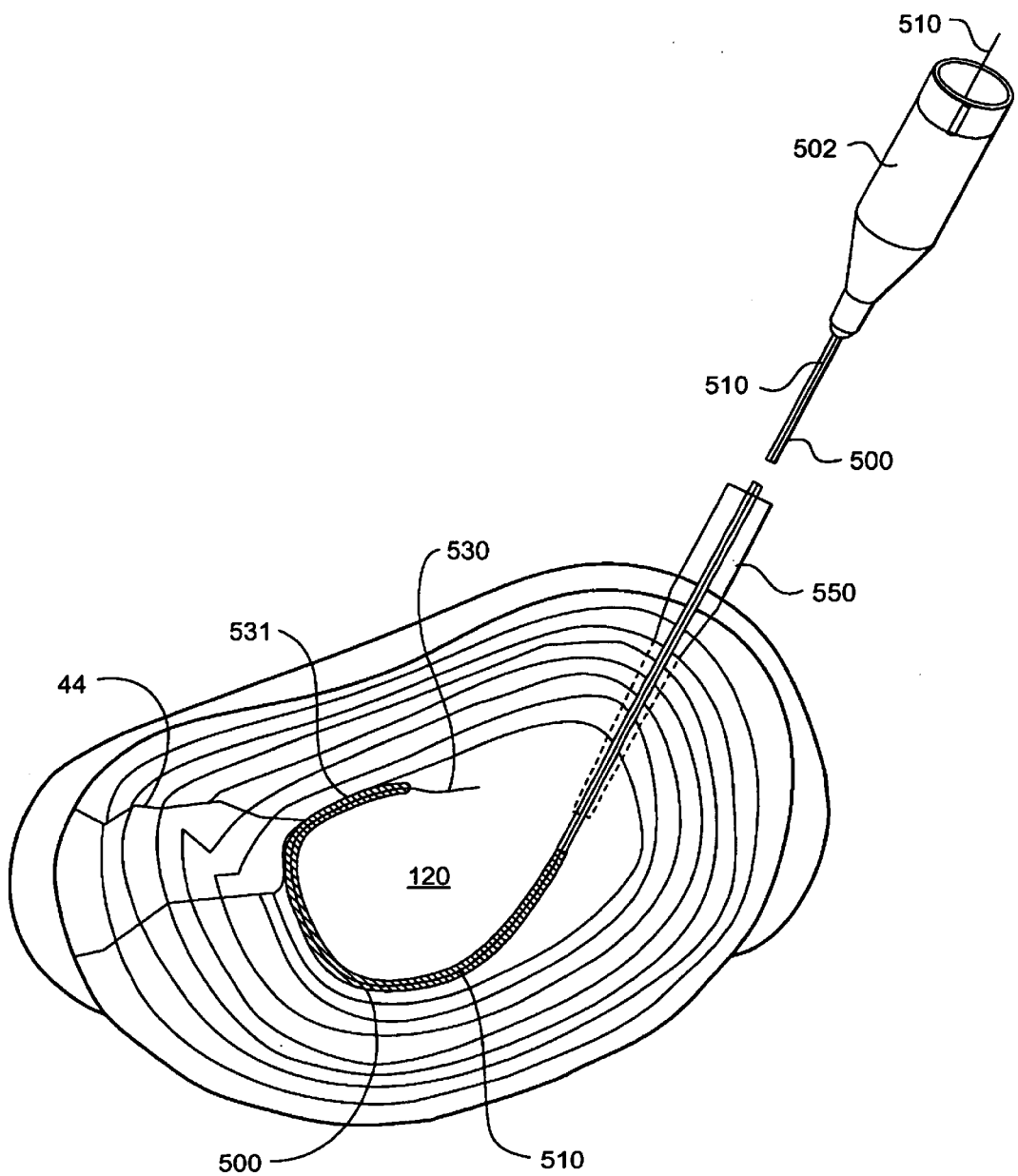
FIG. 5E is a partial cross-sectional view of the guide wire and dialator sheath of FIG. 5D with a treatment catheter inserted over the guide wire to the desired treatment site along the posterior aspect of the intervertebral disc.

In FIG. 5E, the catheter 500 is inserted into the disc through sheath 550. Catheter 500 has a distal portion 531 which is configured to a desired treatment modality and function such as ablation of nucleus pulposus material by the delivery of energy, shrinkage or associated collagen structures near the annular fissure or tear 44 by delivery of energy, suction of extraneous herniated material, delivery of medicaments for the relief of pain associated with a fissure or herniation, insertion of a balloon catheter for expansion of the nuclear material, ultrasound monitoring, visual monitoring of the nucleus or annulus via fiber optic or diagnostic delivery of fluoroscopic solutions. In a preferred embodiment, the catheter 500 includes a heating element at or near the distal portion 531 such that the annular fissure may be treated with thermal energy such that the fissure is sealed. It will be appreciated that the guide wire 510 may remain in place and catheter 500 may be "exchanged" such that different functional catheters as described above may be inserted and withdrawn to perform a specific function or a variety of separate functions. This is advantageous in that the traumatic effect of a percutaneous surgical procedure is limited in that a single surgical site may provide various treatments without the need for multiple surgical sites.

Figure 5F:
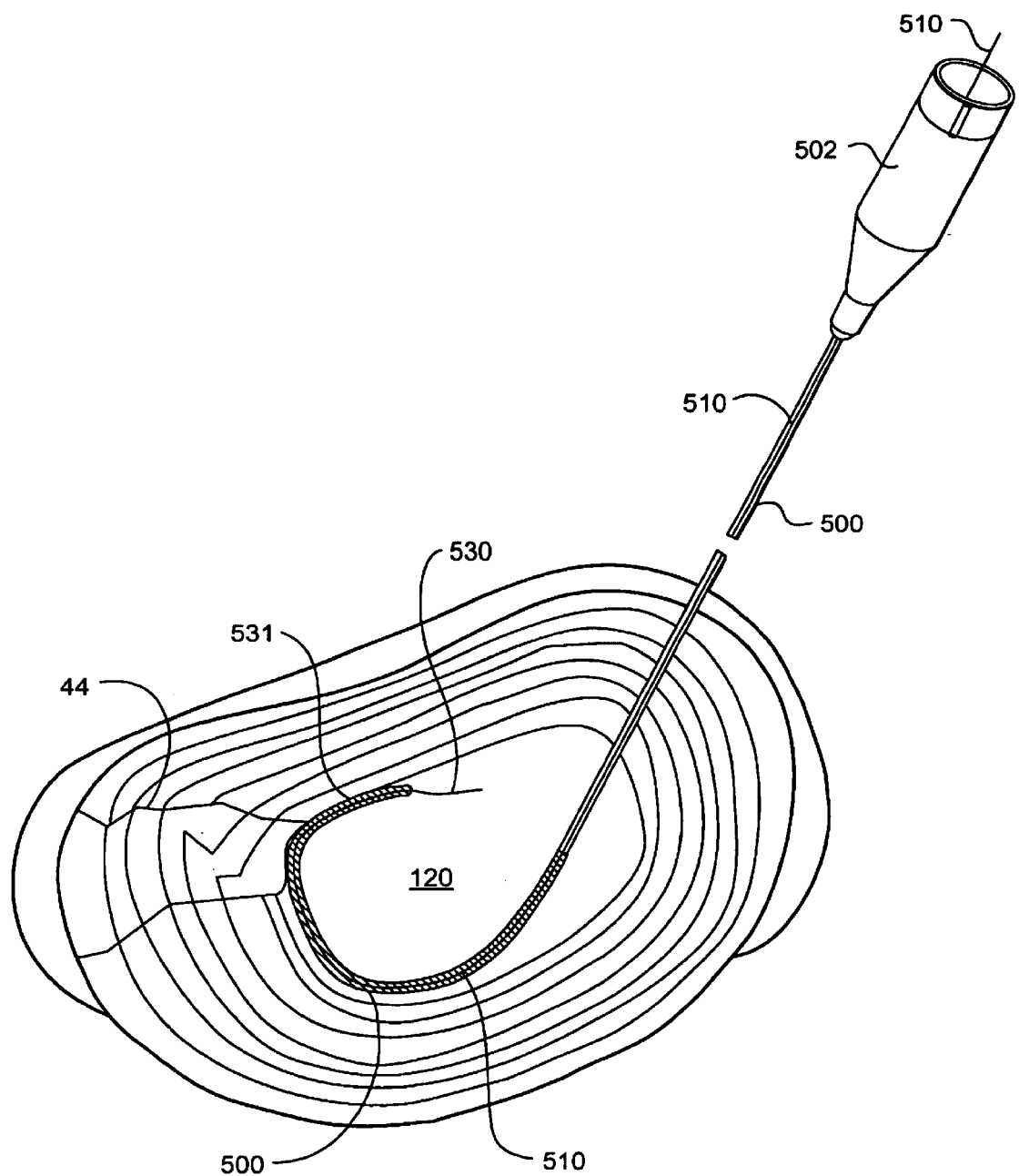
FIG. 5F is a partial cross-sectional view of the guide wire and treatment catheter of FIG. 5E after the sheath is removed.

FIG. 5F illustrates the removal of the sheath 550 of FIG. 5E such that the guide wire 510 remains within the nucleus pulposus and the flexible distal portion remains positioned along the posterior inner wall of the annulus. The catheter 500 remains in place over guide wire 510 and the desired function may be performed along the desired portion of the intervertebral disc.

Figure 5G:
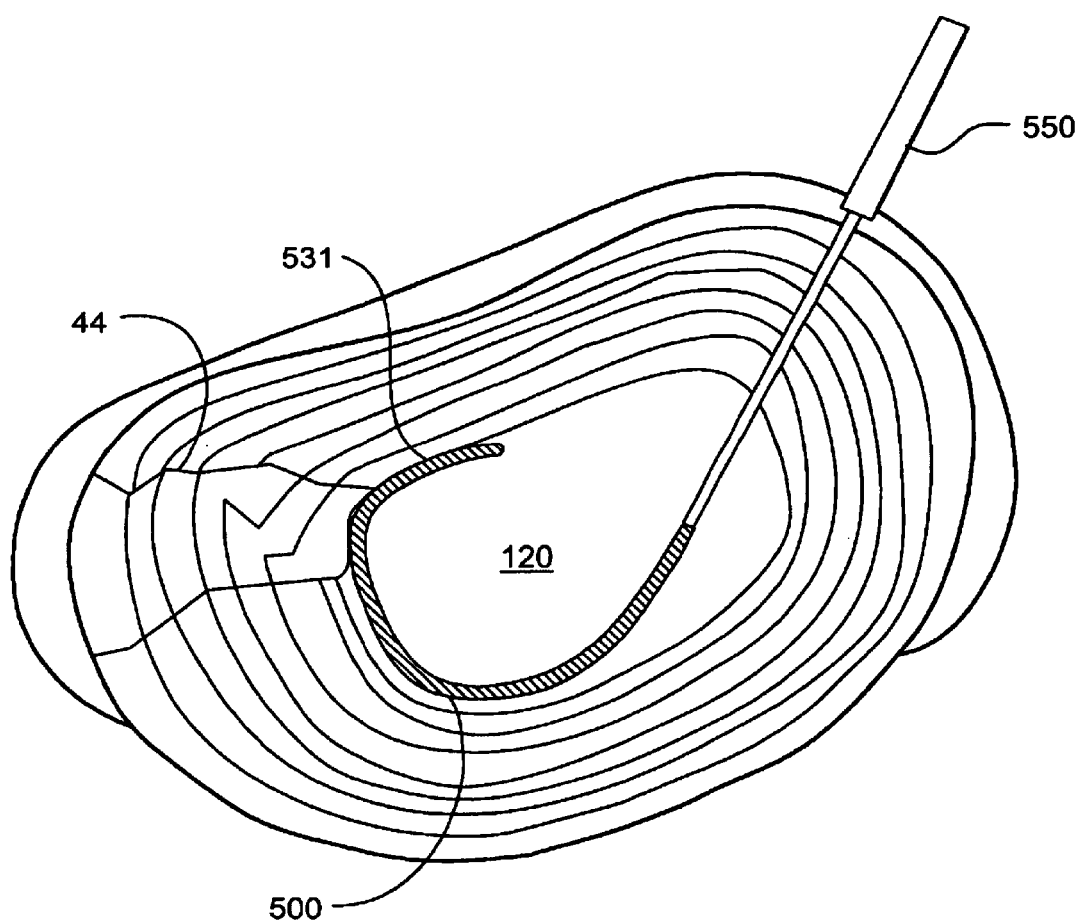
FIG. 5G is a cross-sectional view of a specific embodiment of the apparatus of the present invention wherein the treatment catheter remains within the dialator sheath and the guide wire is removed.

An alternative embodiment of the apparatus of the present invention is illustrated in FIG. 5G. The sheath 550 remains in place percutaneously with catheter 500. The guide wire is removed from the inner lumen of the catheter 500. Distal tip 531 of the catheter remains in place due to the semisolid characteristics of the nucleus pulposus 120. The desired function may still be performed along the inner wall such as at the annular fissure 44.

The materials that make up the various parts of an apparatus of the invention have the following characteristics: the guide wire 510 component has a preferable tensile strength of 600–2000 Mpa. The percent elongation of the guide wire is from 5–100 with a desired geometry of 0.2–2.3 mm. Preferably, there is little conductivity Tensile strength and % elongation can be measured according to ASTME8 (tension test of metallic materials). Conductivity and resistivity can be determined by procedures to be found in ASTM Vol. 2.03 for electrothermal properties. The heating element has at least a 300 Mpa tensile strength with a % elongation of 20%. The conductivity of the heating element is preferably in the range of 0.025–0.2 cal/cm2/cm/sec/C with a resistivity of 500–1500.

The diameter of the guide wire is preferably between 0.0020–0.0050 inches. The actual dimensions of the guide wire will vary with the stiffness and tensile strength of the material used to form the guide wire. The guide wire may also have various other shapes other than tapered or a flattened ribbon such as triangular, oval, wedge or rectangular in cross-sectional shape. The guide wire preferably has a total length greater than or at least equal to the length of the catheter. The guide wire may be manufactured from a high strength alloy containing cobalt, nickel, chromium or to a composite product having a portion formed of an alloy and a pseudoelastic alloy such as NiTi (NITINOL). Other materials include 304 and 316 stainless steel, semi-hard metals, fully hard metals, Elgiloy from Elgiloy Limited Partnership, Haynes 188 from Haynes International and MP35N (a cobalt-nickel alloy) from Carpenter Technology Corporation.

The catheter has a diameter in the range between 0.0020–0.0068 inches with a 0.0038 inch preferred diameter. The catheter sheath is preferably polyimide but may be any biocompatible material such as polyurethane, polyester, rayon, polyamide and silicone. The sheath may be a braided structure such that the flexibility of the catheter may be adjusted by varying the tightness of each braided section. The length of the catheter is in the range of 3.9 inches to 23.6 inches (10 cm to 60 cm, respectively). The interior of the catheter may also be coated such that the outer sheath has support characteristics. Such coatings include but are not limited to silicone, polyimide and the like. The inner lining and coating also provide for a smooth gliding over the guide wire to prevent kinking or snagging of the catheter.

Figure 6A:
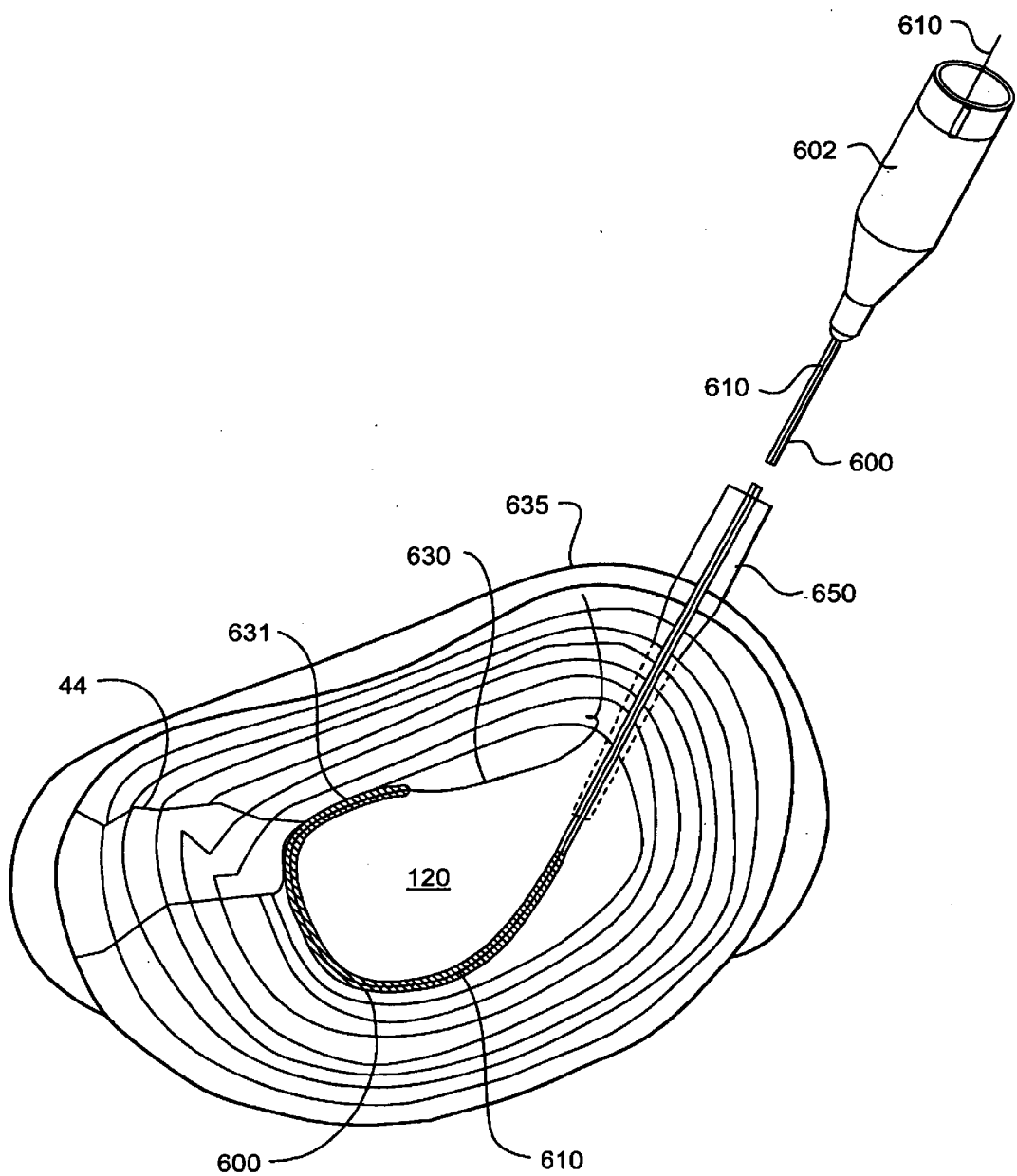
FIG. 6A is a partial cross-sectional view of a specific embodiment of the apparatus of the invention illustrating a guide wire with a distal locking tip within a dialator sheath.
Figure 6B:
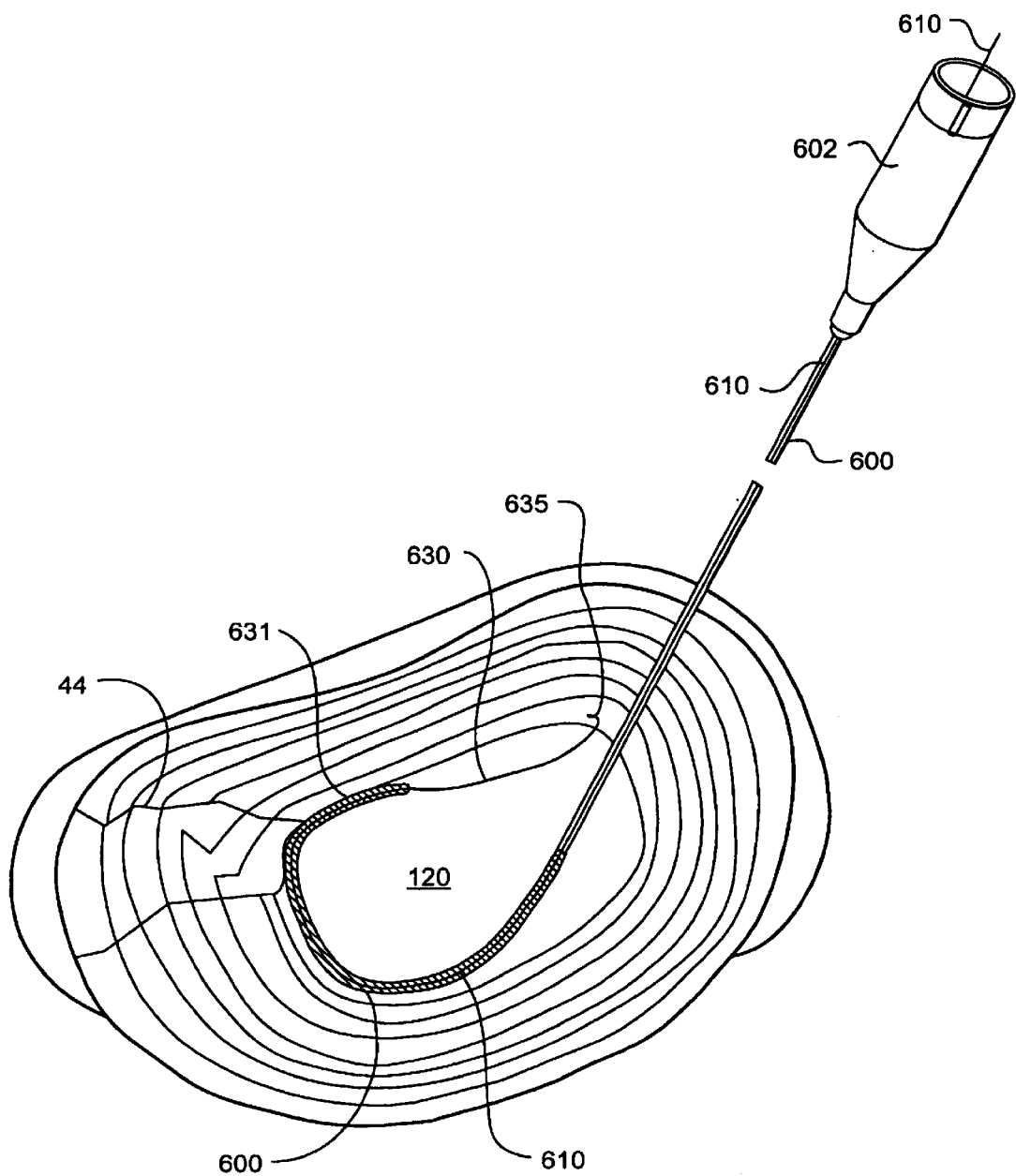
FIG. 6B is a partial cross-sectional view of the apparatus of FIG. 6A with the dialator removed.

Referring to FIG. 6A, a specific embodiment of the core guide wire 610 with a distal hooking tip 635 is illustrated to fix the modular guide wire to the interior annulus wall after final position is achieved. Thus, displacement of the guide wire is prevented during subsequent exchange and withdrawal of other system components. The guide wire 610 is inserted through the introducer (not shown) and navigated to a desired portion along the inner wall of the annulus. Distal locking tip 635 is inserted and held in place such that the distal portion 630 remains in place. The catheter 600 slides through sheath 650 into the nucleus 120 of the intervertebral disc. The distal portion 631 of catheter 600 is positioned at the annular fissure 44 for performing a function as described above. FIG. 6B illustrates the catheter 700 placed within the intervertebral disc with sheath 650 removed.

Figure 7A:
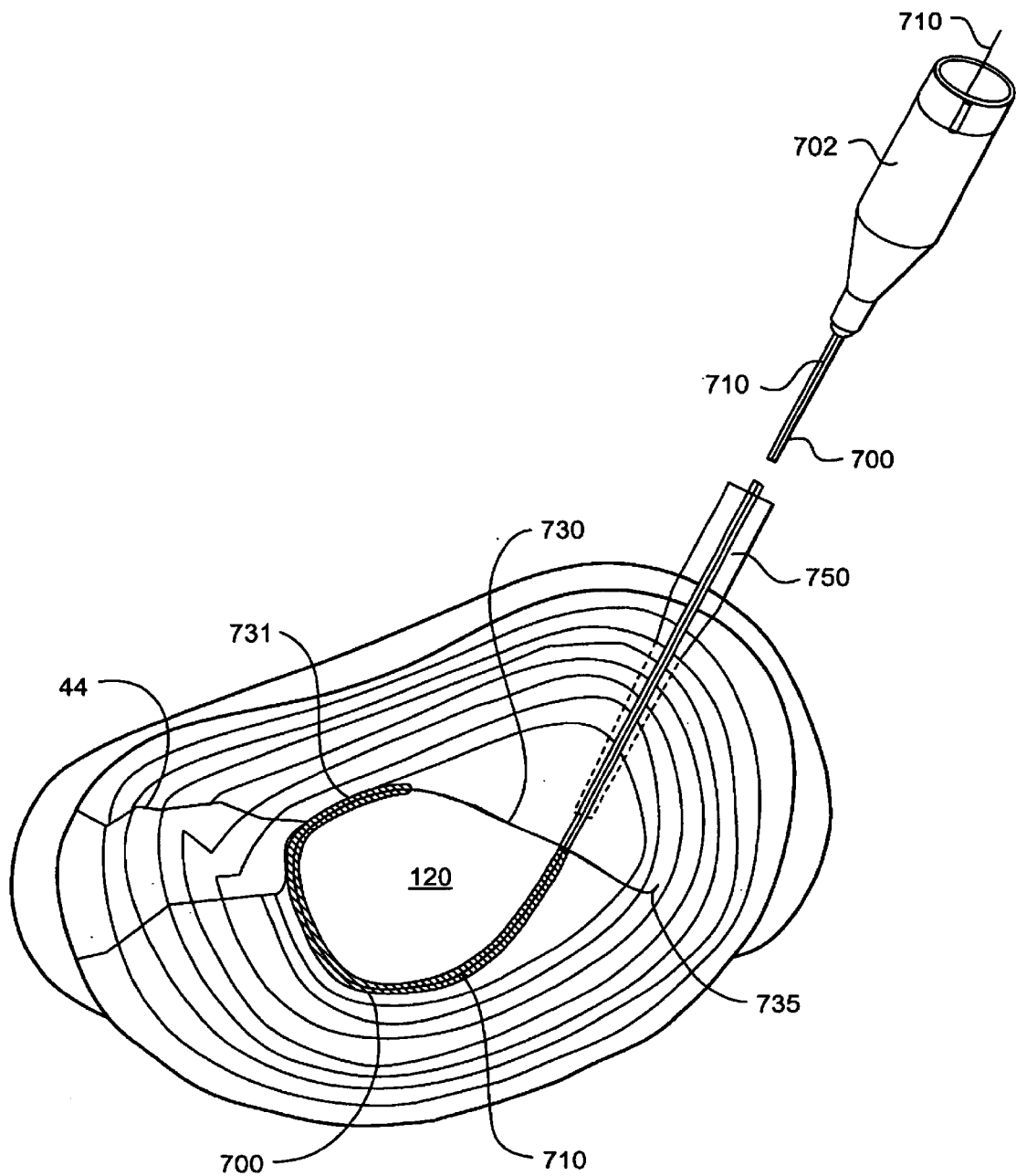
FIG. 7A is a partial cross-sectional view of a specific embodiment of the apparatus according to the present invention illustrating a guide wire with a preformed shape which crosses through the nucleus to lock on an anterior aspect of the intervertebral disc within the dialator.
Figure 7B:
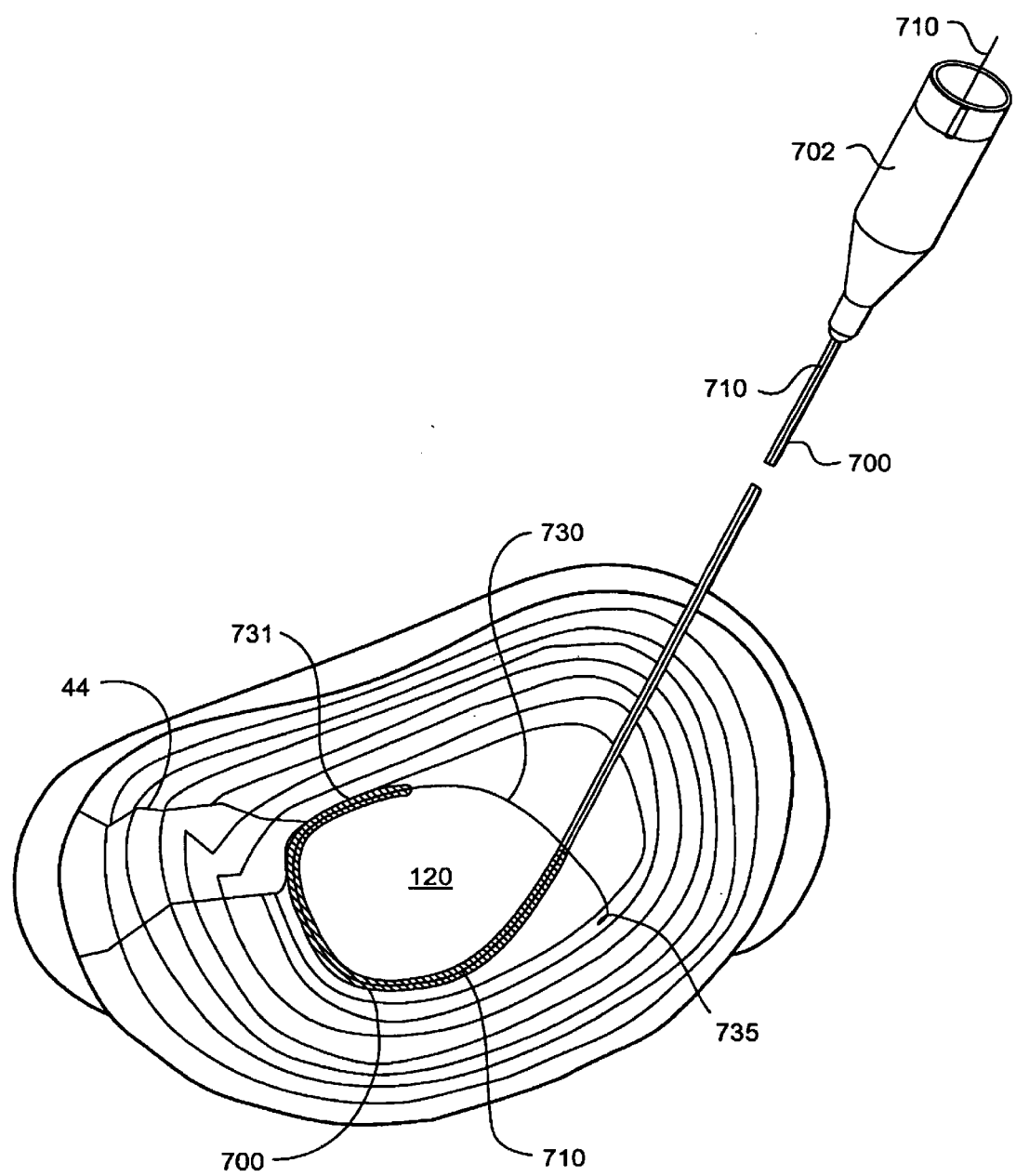
FIG. 7B is a partial cross-sectional view of the apparatus of FIG. 7A illustrating the removal of the dialator.

In another specific embodiment, the guide wire has a cross-locking configuration to fix the modular guide wire to the interior annulus wall. FIG. 7A illustrates a guide wire 710 passing through an introducer sheath 750 and being navigated along the annulus wall and locked into place with distal locking tip 735. Flexible distal portion 730 is crossed-over the guide wire 710 and locked into an anterior portion of the disc. The catheter 700 is slid over the guide wire 710 to place distal portion 731 within the nucleus pulposus along annular fissure 44. FIG. 7B illustrates the catheter 700 in place without the sheath 750.

FIG. 8A depicts one specific embodiment of a catheter 800 over guide wire 810. Guide wire 810 is placed within intervertebral disc 118 and distal portion 830 and distal tip 820 are positioned along the posterior inner wall of the annulus. Sheath 850 is placed into the intervertebral disc 118 for introduction of catheter 800. Distal portion 831 of the catheter 800 is shown over the guide wire 810.

In a detail figure, FIG. 8B illustrates the catheter 800 in cross-section according to the present invention over a section of the guide wire 810. The distal tip 821 of heating catheter 800 has an opening into the lumen 801 for passing over the guide wire 810. The internal lumen near the distal portion 831 contains a heating coil 860 for resistive heating. The heating coil 860 is electrically connected to an electrosurgical generator at the proximal portion of the catheter (not shown). A thermal sensor 870 such as a thermocouple is also positioned at the distal portion 831 of the catheter 800. A potting material can be used to fix the position of the thermal sensor 870 and provide a larger area from which to measure the temperature within the area. The thermal sensor 870 is connected by conductor 872 to a sensor located preferably within the electrosurgical generator but alternately within a separate unit. The sensor is of conventional design, including but not limited to a thermistor, T type thermocouple with copper constantan junction, J type, E type, and K type thermocouples, fiber optics, resistive wires, infrared detectors, integrated circuits and the like. Optionally, there may be a separate lumen for the thermal sensor connection.

FIG. 8C shows a detailed cross-section of the arrangement of the guide wire 810 within catheter 800. Electrical conductor 862 is connected to heating element 860. Thermal sensor 870 is illustrated within the cross-section of the catheter. The arrangement of the conductors, thermal sensors and guide wire within the catheter are meant for illustration only and any suitable arrangement will be appreciated by those skilled in the art.

Figure 9A:
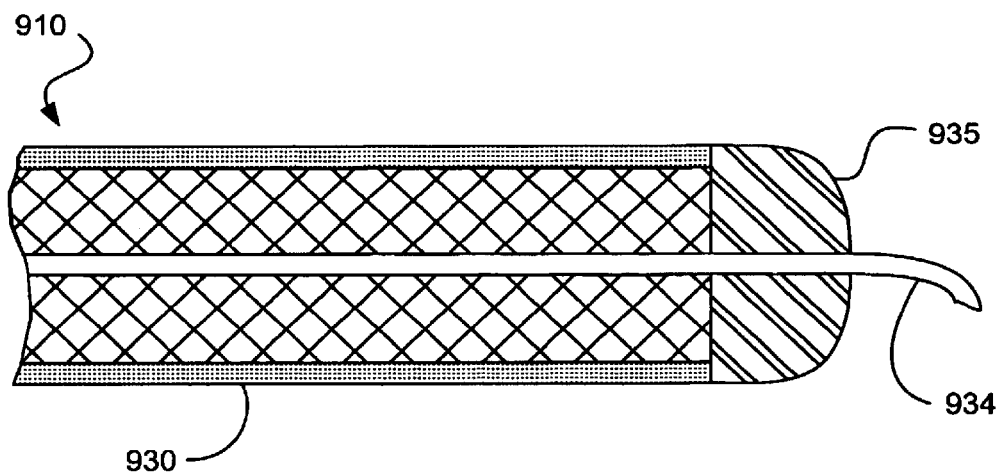
FIG. 9A is a cross-sectional view of a specific embodiment of the distal tip of the guide wire according to the present invention with a hook locking tip.
Figure 9B:
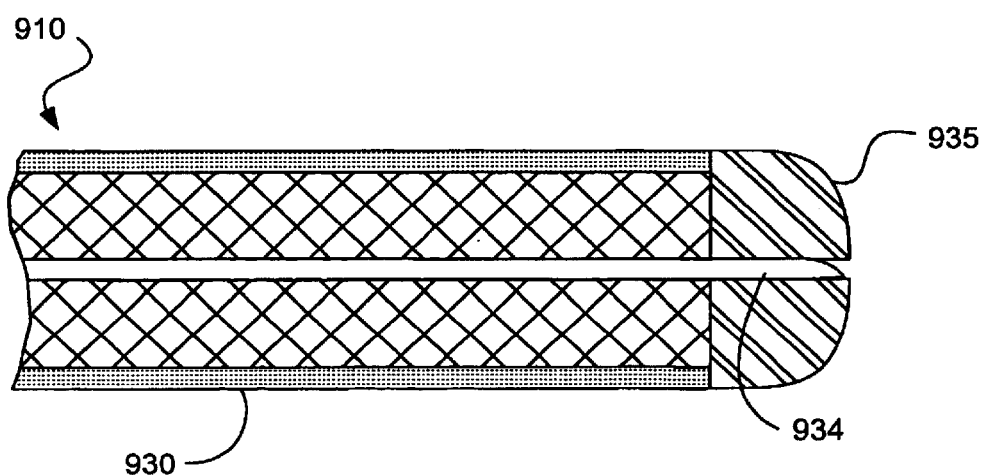
FIG. 9B is a detailed cross-sectional view of the distal tip of the guide wire of FIG. 9A showing the hook locking tip retracted within the distal tip.

FIGS. 9A and 9B illustrate another specific embodiment of a distal tip of a core guide wire according to the invention. Guide wire 910 may be configured to have a locking distal tip 935. Hooking element 934 extends out of distal tip 935 to anchor the tip within the annular wall. FIG. 9B illustrates the hooking element 934 retracted into a lumen within the distal portion 930 of the guide wire 910. The hooking element 934 may be deployed by a slight twisting or push-pull on the guide wire 910 such that the hook engages the annular wall to hold the guide wire.

Figure 10:
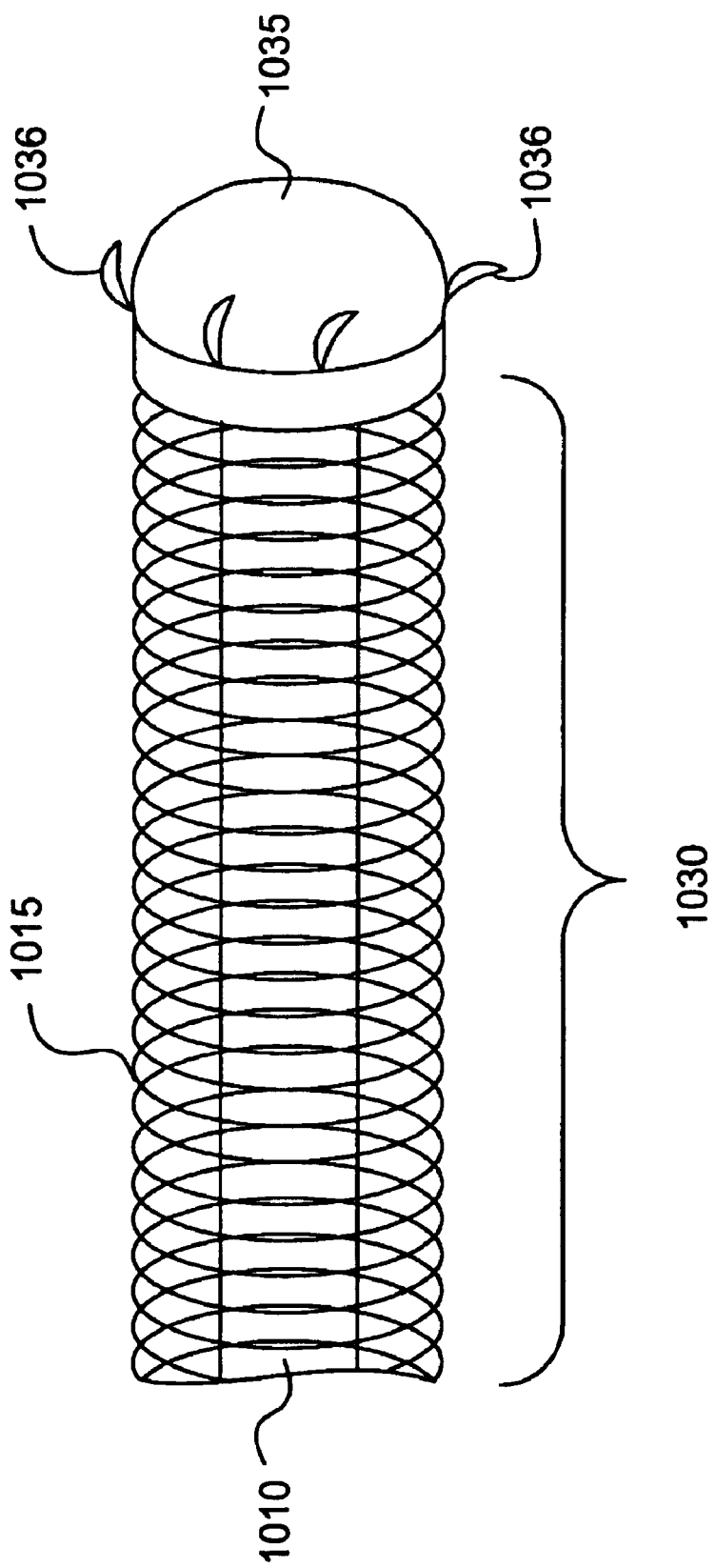
FIG. 10 is a plan view of a specific embodiment of the guide wire of the present invention with a coil at the distal flexible portion and a directional hook locking tip.

FIG. 10 is another specific embodiment of the present invention with a substantially constant diameter core guide wire 1010 with a flexible distal portion 1030. The flexible distal portion further has coils 1015 for added flexibility at the distal tip. Distal tip 1035 is a locking tip with hooks 1036 along an edge of the distal tip. The hooks 1036 are oriented such that a clockwise twist of the guide wire 1010 will lock the tip into the annulus inner wall. A counterclockwise twist will release the guide wire from being locked.

Figure 11:
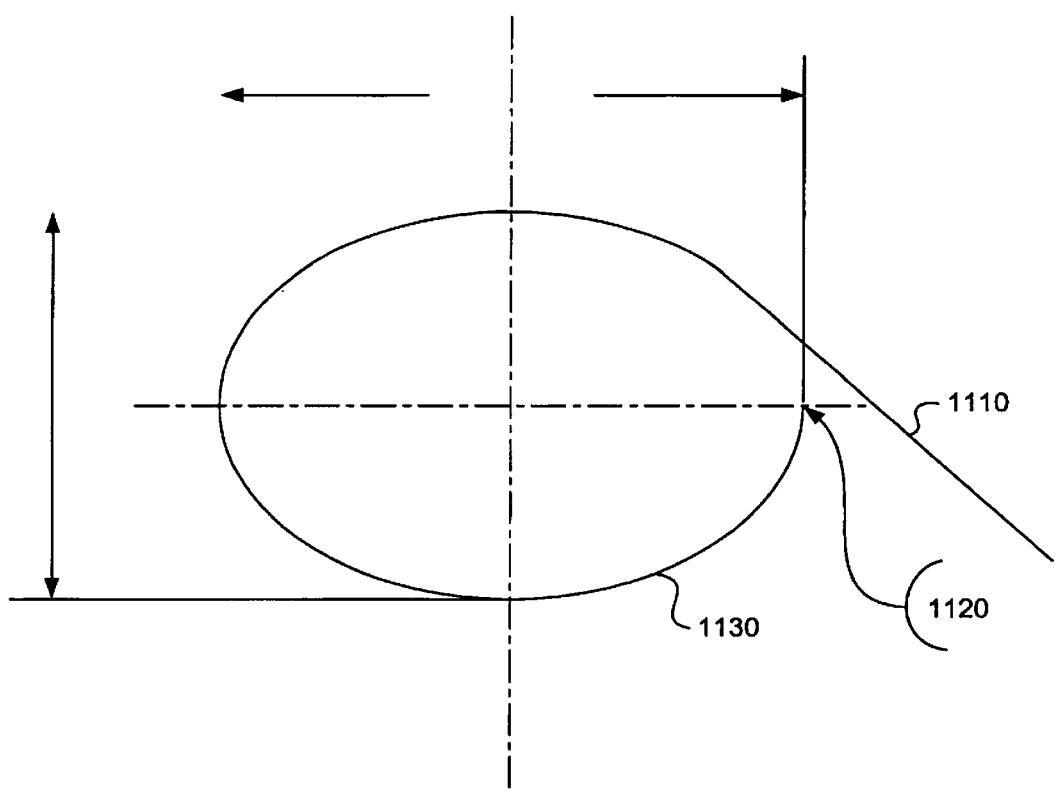
FIG. 11 is a simplified plan view of a guide wire using a pre-shaped form to retain a curved shape after deployment.

In FIG. 11, the shaped memory characteristics of the guide wire are illustrated. The guide wire 1110 is substantially straight along a proximal portion of the core wire. The distal portion 1130 is pre-shaped into a curve shaped such that the distal tip 1120 will curve toward the guide wire after deployment such as in the cross-locking embodiment describe above in FIG. 7A. It will be appreciated that any pre-shaped configuration may be used to define the distal portion of the guide wire.

Turning now to FIG. 12, various thermal energy elements are illustrated. The thermal energy element may be positioned around an exterior of the catheter or within the lumen of the catheter as depicted in FIG. 8B. For instance, the thermal energy element may be an integrated structural element with the catheter sheath or the element may be separately constructed as a circuit and mounted to the catheter by epoxy or other attachment method known within the art. The thermal energy element may also be biased in that the element may be mounted differentially along one side of the catheter such that a preferential treating occurs substantially along only a portion of the catheter. Suitable materials for the heating element include but are not limited to stainless steel, NITINOL, nickel/chromium allows, platinum and the like. The heating element may also be a polymeric structure with differing flex characteristics to provide some support to the catheter near the distal tip.

In one embodiment, the thermal energy element 1260 is a resistive heating coil. The resistive material is electrically insulated and substantially no current escapes into the body. With increasing levels of current, element 1260 may heat the annulus to greater temperature levels without a change in the structure of the coil. A specific embodiment of a temperature level is approximately 55 C at a specific target site such as an annular fissure. The range for heat is from 45 C to 75 C.

Figure 12A:
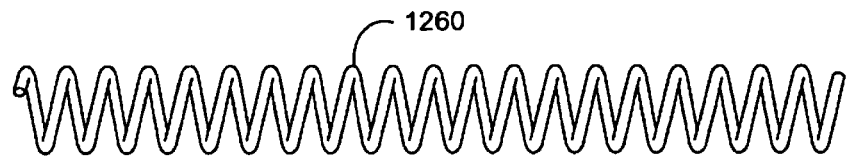
FIG. 12A is a plan view of the heating element of the treatment catheter of FIG. 8B with a helical coil structure.
Figure 12B:
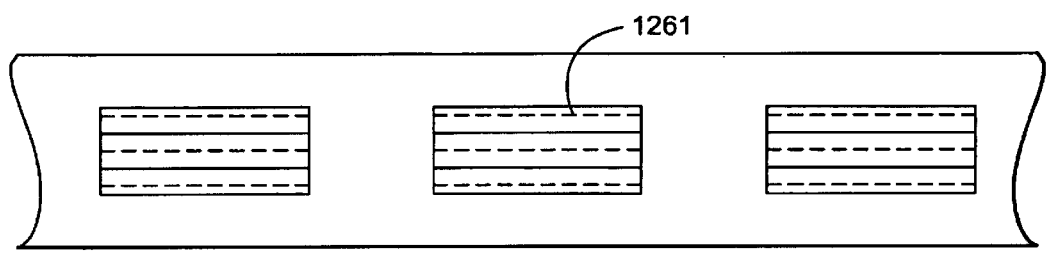
FIG. 12B is a plan view of a specific embodiment of the heating element of the catheter of FIG. 8B with a flat structure.
Figure 12C:
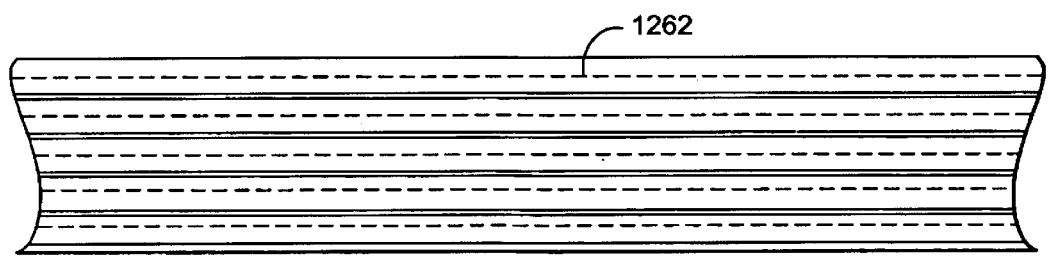
FIG. 12C is a plan view of a specific embodiment of the heating element of the catheter of FIG. 8B with a ribbon structure.

In another embodiment, sufficient energy is delivered to the intervertebral disc to heat and shrink the collage component of the annulus fibrosus and/or nucleus pulposus but not to ablate any surrounding tissue adjacent to the catheter. The heating coil is configured to seal the fissure without damage to surrounding tissue. It is believed that the injury to the intervertebral disc tissue and the body's own healing response leads to a marked improvement FIG. 12B illustrates a heating element 1261 which is a flat element. The flat elements may be etched onto a surface of the catheter or separate element to be bonded to the catheter by chemical etching, electrochemical etching, photo etching or physical etching. Additionally, the flat heating elements 1261 may be chemically, electrically or physically deposited onto the surface. Similarly, in FIG. 12C, the heating element may be in the form of a flex ribbon heating element 1262. Each heating element 1261 may be individually connected to the electrosurgical generator to deliver power and energy either in parallel or series such that the energy is delivered between each element and through the tissue.

Figure 12D:
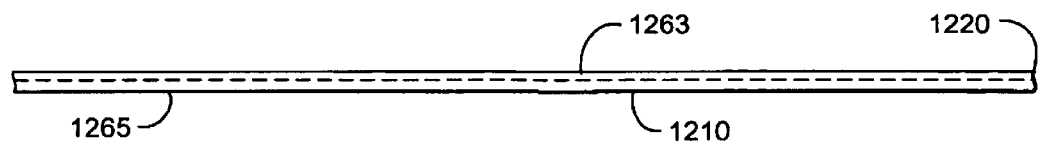
FIG. 12D is a plan view of a specific embodiment of the heating element of the catheter of FIG. 8B using a distal portion of the guide wire as a monofilament heating element.

In another specific embodiment, FIG. 12D illustrates a heating element comprised of a section of the core guide wire 1210 in the form of a monofilament 1263. A proximal portion 1265 of the guide wire has insulation to prevent heating of the guide wire at that portion. Distal portion 1220 is used as the heating element to deliver thermal energy to the desired site.

Additionally, a radiographically opaque marking device can be included in the distal portion of the catheter (such as in the tip or at spaced locations throughout the intradiscal portion) so that advancement and positioning of the intradiscal section can be directly observed by radiographic imaging. Such radiographically opaque markings are preferred when the intradiscal section is not clearly visible by radiographic imaging, such as when the majority of the catheter is made of plastic instead of metal. A radiographically opaque marking can be any of the known (or newly discovered) materials or devices with significant opacity. Examples include but are not limited to a steel mandrel sufficiently thick to be visible on fluoroscopy, a tantalum/polyurethane tip, a gold-plated tip, bands of platinum, stainless steel or gold, soldered spots of gold and polymeric materials with radiographically opaque filler such as barium sulfate. A resistive heating element or a RF electrode(s) may provide sufficient radio-opacity in some embodiments to serve as a marking device.

In a specific embodiment, temperatures delivered through the heating element may be detected at sensors to provide feedback for maintaining a selected power in the electrosurgical generator. The actual temperatures are measured at a temperature measurement device, and the temperatures are displayed at a user interface and display. A control signal is generated by a controller that is related to the actually measured temperature and a desired temperature. The control signal is used by power circuits to adjust the power output in an appropriate amount in order to maintain the desired temperature delivered at the respective sensor. A multiplexer can be included to measure current, voltage, and temperature at the sensors so that appropriate energy can be delivered to resistive heating elements.

It will also be appreciated by one skilled in the art that the core of the guide wire can also provide the function of differential flexibility by varying the thickness in one or more dimensions (for example, the "thin" dimension, the "thick" dimension, or both) along the length of the guide wire. A guide wire that tapers (becomes gradually thinner) toward the distal tip of the guide wire will be more flexible and easier to bend at the tip than it is at other locations along the guide wire. A guide wire that has a thicker or more rounded tip than more proximal portions of the mandrel will resist bending at the tip but aid bending at more proximal locations. Thickening (or thinning) can also occur in other locations along the guide wire. Control of the direction of bending can be accomplished by making the guide wire more round, i.e., closer to having 1:1 diameter ratios; flatter in different sections of the guide wire; or by varying the absolute dimensions (increasing or decreasing the diameter). Such control over flexibility allows instruments within a catheter over the guide wire to be designed that minimize bending in some desired locations (such as the location of connector of an electrical element to avoid disruption of the connection) while encouraging bending in other locations (e.g., between sensitive functional elements). In this manner, a guide wire that is uniformly flexible along its entire length, is variably flexible along its entire length, or has alternating more flexible and less flexible segment(s), is readily obtained simply by manufacturing the guide wire with appropriate thickness at different distances and in different orientations along the length of the guide wire. Such a catheter will have two or more different radii of curvature in different segments of the guide wire and catheter under the same bending force.

Some characteristics of alternative guide wires include steerability with a 1:1 torque response; formability with a ribbon to allow the physician to shape a "J" curve on the tip. The guide wire also has flexible characteristics in order to negotiate tortuous anatomy and tight lesions without damaging the guide wire or associated catheter. The guide wire may also be tracked so that a balloon catheter is able to move over the wire with minimum resistance. The guide wire is also preferably radiopaque so as to be visible under fluoroscopy.

The foregoing description of specific embodiments of the invention have been presented for purposes of illustration and description. They are not intended to be exhaustive or to limit the invention to the precise forms disclosed. Obviously, many modifications and variations will be apparent to practitioners skilled in this art. The embodiments were chosen and described in order to best explain the principles of the inventions and its practical application, to thereby enable others skilled in the art to best utilize the invention and various embodiments with various modifications as are suited to the particular use contemplated. It is intended that the scope of the invention be defined by the following claims and their equivalents.

What is claimed is:

1. An apparatus for accessing a selected section of an intervertebral disc comprising:
   a catheter having a lumen; and
   a guide wire having a distal portion and a proximal portion, and configured to be positioned within and moved relative to the lumen of the catheter, wherein the guide wire is capable of navigating itself within an intradiscal section of an intervertebral disc to a selected section of the disc and the catheter is capable of being advanced relative to the guide wire such that the catheter follows a path of the guide wire within the intradiscal section of the disc adjacent an inner wall of an annulus of the disc to the selected section, wherein the guide wire has (a) sufficient rigidity to be advanceable through a nucleus pulposus and the annulus fibrosus under a force applied longitudinally to the proximal portion of the guide wire, and (b) insufficient penetration ability to be advanceable out through the annulus fibrosus under the applied force.

2. The apparatus according to claim 1, wherein the guide wire has sufficient flexibility in a direction of a disc place to be compliant with an inner wall of the annulus of the disc.

3. The apparatus according to claim 1, wherein the distal portion of the guide wire includes a spring coil.

4. The apparatus according to claim 3, wherein the spring coil contains a forming ribbon.

5. The apparatus according to claim 1, wherein the distal portion of the guide wire is tapered to a smaller diameter toward the distal end.

6. The apparatus according to claim 1, wherein the distal portion of the guide wire has a distal tip at the extremity of the distal portion of the guide wire.

7. The apparatus of claim 6, wherein the distal tip is configured to be non-piercing through an annulus fibrosus.

8. The apparatus according to claim 6, wherein the distal tip is a blunt tip.

9. The apparatus according to claim 6, wherein distal tip is a rolling ball tip.

10. The apparatus according to claim 1, wherein the distal portion of the guide wire includes a locking mechanism for securing the guide wire within the selected section of the disc, the locking mechanism including a piercing tip.

11. The apparatus according to claim 10, wherein the locking mechanism includes a retractable hook.

12. The apparatus according to claim 10, wherein the locking mechanism includes a plurality of directional hooks.

13. The apparatus according to claim 12, wherein the plurality of directional hooks are configured to secure the guide wire within the selected section of the disc by rotating the hooks in a first direction, and to release the guide wire from the selected section of the disc by rotating the hooks in a second direction that is substantially opposite to the first direction.

14. The apparatus according to claim 10, wherein the guide wire is capable of cross-locking itself once the guide wire is advanced to the selected section of the disc.

15. The apparatus according to claim 12, wherein the locking mechanism comprises a hook.

16. The apparatus according to claim 12, wherein the distal portion of the guide wire forms the locking mechanism.

17. The apparatus of claim 12, wherein the distal portion of the guide wire has a distal tip that includes the piercing tip.

18. The apparatus according to claim 12, wherein the piercing tip is configured to secure the guide wire by piercing the selected section of the disc.

19. The apparatus according to claim 12, wherien the piercing tip is configured to secure the guide wire against movement in all directions.

20. The apparatus according to claim 1, wherein the proximal portion of the guide wire has an outer diameter between about 0.005–0.025 inches.

21. The apparatus according to claim 1, wherein the distal portion of the guide wire has an outer diameter between about 0.002–0.012 inches.

22. The apparatus according to claim 1, wherein the proximal portion of the guide wire is between about 10–15 inch long.

23. The apparatus according to claim 1, wherein the distal portion of the guide wire is between about 0.2–1.2 inch long.

24. The apparatus of claim 1, wherein the distal portion of the guide wire has a length at least one-half of a diameter of the nucleus pulposus.

25. The apparatus of claim 1, wherein the apparatus further comprises a dialator sheath configured to be slid over the guide wire for introducing the catheter onto the guide wire.

26. The apparatus of claim 1, wherein at least a portion of the guide wire is actively steerable.

27. The apparatus of claim 1, wherein at least a portion of guide wire is radiographically visible.

28. The apparatus of claim 1, wherein the distal portion of the guide wire has one or more flat sides.

29. The apparatus of claim 1, wherein the guide wire has a bending stiffness as measured in Taber stiffness units between about 2–400 units in a desired bending plane.

30. The apparatus of claim 1, wherein the guide wire has a bending stiffness as measured in Taber stiffness units between about 3–150 units in a desired bending plane.

31. The apparatus of claim 1, wherein the distal portion of the guide wire has a column strength between about 0.2–7 kg.

32. The apparatus of claim 1, wherein the distal portion of the guide wire has a column strength between about 0.7–4 kg.

33. The apparatus of claim 1, wherein the catheter further includes a functional element for performing a function adjacent the selected section.

34. The apparatus of claim 33, wherein the function is selected from the group consisting of delivering energy, adding material and removing material.

35. The apparatus of claim 33, wherein the functional element comprise a thermal energy delivery device.

36. The apparatus of claim 35, wherein a thermal energy source is operably attached to the thermal energy delivery device through the catheter.

37. The apparatus of claim 35, wherein the thermal energy delivery device is selected from the group consisting of microwave probe, optical fiber, radio frequency electrode and ultrasound emitter.

38. The apparatus of claim 35, wherein the thermal energy delivery device is a resistive heater.

39. The apparatus of claim 35, wherein the catheter further comprises at least one sensor capable of monitoring temperature, power, voltage or a combination thereof and the input from the sensor controls energy supplied to the thermal energy device.

40. The apparatus of claim 33, wherein the functional element comprises an irrigation lumen extending from a proximal end of the catheter to the intradiscal section.

41. The apparatus of claim 33, wherein the functional element is capable of delivering a controlled amount of energy at or near the fissure such that no vaporization occurs at or near the fissure when energy is delivered by the functional element.

42. The apparatus of claim 33, wherein the functional element is capable of delivering a controlled amount of energy at or near the fissure such that no material other than water is removed at or near the fissure when energy is delivered by the functional element.

43. The apparatus of claim 33, wherein the functional element is capable of delivering a controlled amount of energy at or near the fissure such that no destructive lesion is formed on a disc at or near the fissure when energy is delivered by the functional element.

44. An apparatus for accessing a selected section of an intervertebral disc comprising:

a catheter having a lumen; and a guide wire having a distal portion and a proximal portion, and configured to be positioned within and moved relative to the lumen of the catheter, wherein the guide wire is capable of navigating itself within an intradiscal section of an intervertebral disc to a selected section of the disc and the catheter is capable of being advanced relative to the guide wire such that the catheter follows a path of the guide wire within the intradiscal section of the disc adjacent an inner wall of an annulus of the disc to the selected section, wherein the guide wire has sufficient flexibility in a direction of a disc plane to be compliant with the inner wall of the annulus of the disc.

45. An apparatus for accessing a selected section of an intervertebral disc comprising:

a catheter having a lumen; and a guide wire having a distal portion and a proximal portion, and configured to be positioned within and moved relative to the lumen of the catheter, wherein the guide wire is capable of navigating itself within an intradiscal section of an intervertebral disc to a selected section of the disc and the catheter is capable of being advanced relative to the guide wire such that the catheter follows a path of the guide wire within the intradiscal section of the disc adjacent an inner wall of an annulus of the disc to the selected section, wherein the distal portion of the guide wire has a rolling ball tip at the extremity of the distal portion of the guide wire.

46. An apparatus for accessing a selected section of an intervertebral disc comprising:

a catheter having a lumen; and a guide wire having a distal portion and a proximal portion, and configured to be positioned within and moved relative to the lumen of the catheter, wherein the guide wire is capable of navigating itself within an intradiscal section of an intervertebral disc to a selected section of the disc and the catheter is capable of being advanced relative to the guide wire such that the catheter follows a path of the guide wire within the intradiscal section of the disc adjacent an inner wall of an annulus of the disc to the selected section, wherein the guide wire has a middle portion disposed between the proximal and distal portions, and the middle portion is more flexible than both the proximal portion and the distal portion.

47. An apparatus for accessing a selected section of an intervertebral disc comprising:

a catheter having a lumen; and a guide wire having a distal portion and a proximal portion, and configured to be positioned within and moved relative to the lumen of the catheter, wherein the guide wire is capable of navigating itself within an intradiscal section of an intervertebral disc to a selected section of the disc and the catheter is capable of being advanced relative to the guide wire such that the catheter follows a path of the guide wire within the intradiscal section of the disc adjacent an inner wall of an annulus of the disc to the selected section, wherein the guide wire has a middle portion disposed between the proximal and distal portions, and the middle portion is less flexible than both the proximal portion and the distal portion.

48. An apparatus for accessing a selected section of an intervertebral disc comprising:

a guide wire having a distal portion and a proximal portion, the guide wire being capable of navigating itself within an intradiscal section of an intervertebral disc to a selected section of the disc along a path at least partially adjacent an inner wall of an annulus of the disc, wherein the guide wire has (a) sufficient rigidity to be advanceable through a nucleus pulposus and the annulus fibrosus under a force applied longitudinally to the proximal portion of the guide wire, and (b) insufficient penetration ability to be advanceable out through the annulus fibrosus under the applied force.

* * * * *